US011083117B2

(12) United States Patent
Elizondo, II

(10) Patent No.: US 11,083,117 B2
(45) Date of Patent: *Aug. 3, 2021

(54) MODULAR MEDICAL ARTICLE STORAGE CONTAINER WITH TORTUOUS PATH SEAL

(71) Applicant: MEPS Real-Time, Inc., Carlsbad, CA (US)

(72) Inventor: Paul M. Elizondo, II, Escondido, CA (US)

(73) Assignee: MEPS Real-Time, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/833,450

(22) Filed: Mar. 27, 2020

(65) Prior Publication Data

US 2020/0296865 A1 Sep. 17, 2020

Related U.S. Application Data

(63) Continuation of application No. 16/174,208, filed on Oct. 29, 2018, now Pat. No. 10,609,845, which is a (Continued)

(51) Int. Cl.
*G06K 7/08* (2006.01)
*H05K 9/00* (2006.01)
(Continued)

(52) U.S. Cl.
CPC .......... *H05K 9/0009* (2013.01); *A61B 50/18* (2016.02); *A61B 50/33* (2016.02); *G06F 1/182* (2013.01);
(Continued)

(58) Field of Classification Search
CPC ........ A61B 2050/105; A61B 2050/185; A61B 50/18; A61B 50/33; G06F 1/182;
(Continued)

(56) References Cited

U.S. PATENT DOCUMENTS 3,260,788 A  7/1966 Stetson
4,069,618 A  1/1978 Geiss
(Continued)

FOREIGN PATENT DOCUMENTS

EP  0269206 A1  8/1988
EP  0291597 A1  11/1988
(Continued)

*Primary Examiner* — Thien M Le
(74) *Attorney, Agent, or Firm* — Thomas A. Runk; Brooks Kushman P.C.

(57) ABSTRACT

A modular system of plastic walls having embedded and coextensive electrically conductive components configured to electrically connect with each other when the walls are mated. The walls have joining edges that form joint seams with other walls when joined together to create an enclosure. When enough walls are used to surround a storage space, a Faraday cage is created. The walls additionally have portions of tortuous paths at each joining edge that mate with a complementary portion of a tortuous path of another wall when the walls are joined together. A torturous path seal is thereby created at each joint seam. The plastic walls can be configured in a multiplicity of combinations to create various enclosures necessary for RFID-enabled storage and tracking of medical articles. Containers, enclosures, cabinets, and drawers of differing heights and sizes can be made and they may be stacked or otherwise assembled.

32 Claims, 17 Drawing Sheets

Related U.S. Application Data continuation of application No. 15/394,788, filed on Dec. 29, 2016, now Pat. No. 10,117,365.

(60) Provisional application No. 62/273,421, filed on Dec. 30, 2015.

(51) Int. Cl.
| | |
|---|---|
| *G06F 1/18* | (2006.01) |
| *H01L 23/552* | (2006.01) |
| *A61B 50/33* | (2016.01) |
| *A61B 50/18* | (2016.01) |
| *G06K 7/10* | (2006.01) |
| *A61B 50/10* | (2016.01) |

(52) U.S. Cl.
CPC ........ *G06K 7/10316* (2013.01); *H01L 23/552* (2013.01); *H05K 9/009* (2013.01); *H05K 9/0015* (2013.01); *H05K 9/0081* (2013.01); *A61B 2050/105* (2016.02); *A61B 2050/185* (2016.02); *H05K 9/0007* (2013.01); *H05K 9/0032* (2013.01); *Y10S 277/92* (2013.01)

(58) Field of Classification Search
CPC .............. G06K 7/10316; H01L 23/552; H05K 9/0007; H05K 9/009; H05K 9/0015; H05K 9/0032; H05K 9/0081; H05K 9/009; Y10S 277/92

See application file for complete search history.

(56) References Cited

U.S. PATENT DOCUMENTS

| | | | |
|---|---|---|---|
| 4,180,179 A | 12/1979 | Hoenig | |
| 4,711,361 A | 12/1987 | Mischenko | |
| 4,826,718 A | 5/1989 | Unsworth | |
| 5,095,177 A | 3/1992 | Johnson | |
| 5,265,273 A | 11/1993 | Goodwin et al. | |
| 5,405,587 A * | 4/1995 | Fernandez | A61L 2/18 |
| | | | 134/186 |
| 5,456,698 A | 10/1995 | Byland et al. | |
| 5,704,508 A | 1/1998 | Keip | |
| 5,774,344 A | 6/1998 | Casebolt | |
| 6,011,504 A | 1/2000 | Tan | |
| 6,320,121 B1 | 11/2001 | Honeycutt | |
| 7,995,355 B2 | 8/2011 | Cochrane | |
| 8,770,479 B1 | 7/2014 | Shoenfeld | |
| 8,925,251 B1 | 1/2015 | Rust | |
| 2002/0164265 A1 * | 11/2002 | Hetzler | A61L 2/04 |
| | | | 422/26 |
| 2003/0028094 A1 | 2/2003 | Kumar et al. | |
| 2004/0264155 A1 | 12/2004 | Soule | |
| 2005/0158653 A1 * | 7/2005 | Hatakeyama | H01J 37/285 |
| | | | 430/270.1 |
| 2006/0016897 A1 * | 1/2006 | Yasuda | A61B 90/98 |
| | | | 235/492 |
| 2006/0278629 A1 | 12/2006 | Gagas et al. | |
| 2007/0019368 A1 | 1/2007 | Soule et al. | |
| 2007/0109130 A1 | 5/2007 | Edenfield | |
| 2008/0233426 A1 | 9/2008 | Gaviglia | |
| 2009/0183912 A1 | 7/2009 | Hogan | |
| 2010/0063838 A1 * | 3/2010 | Schumacher | G06Q 99/00 |
| | | | 705/2 |
| 2010/0096180 A1 | 4/2010 | Carducci | |
| 2010/0126766 A1 | 5/2010 | Lynam | |
| 2010/0132999 A1 | 6/2010 | Teo et al. | |
| 2010/0200288 A1 | 8/2010 | Cochrane | |
| 2010/0238362 A1 | 9/2010 | Hughes et al. | |
| 2012/0049700 A1 | 3/2012 | Cochrane | |
| 2013/0042556 A1 | 2/2013 | Armijo | |
| 2013/0281596 A1 * | 10/2013 | Mohan | C08L 23/02 |
| | | | 524/427 |
| 2013/0289637 A1 * | 10/2013 | Amely-Velez | A61N 1/3968 |
| | | | 607/5 |
| 2014/0008119 A1 | 1/2014 | Brandt | |
| 2014/0078677 A1 | 3/2014 | Dolci | |
| 2014/0202905 A1 | 7/2014 | Kamath | |
| 2014/0203020 A1 * | 7/2014 | Trombino | A45C 13/18 |
| | | | 220/500 |
| 2015/0096799 A1 | 4/2015 | Frana | |
| 2015/0158653 A1 | 6/2015 | Trombino | |
| 2016/0330503 A1 | 11/2016 | Testin et al. | |
| 2017/0196128 A1 | 7/2017 | Elizondo, II | |

FOREIGN PATENT DOCUMENTS

| | | |
|---|---|---|
| EP | 0452701 A1 | 10/1991 |
| EP | 2160084 A1 | 3/2010 |
| WO | 2011049525 A1 | 4/2011 |
| WO | 2011100356 A1 | 8/2011 |

* cited by examiner

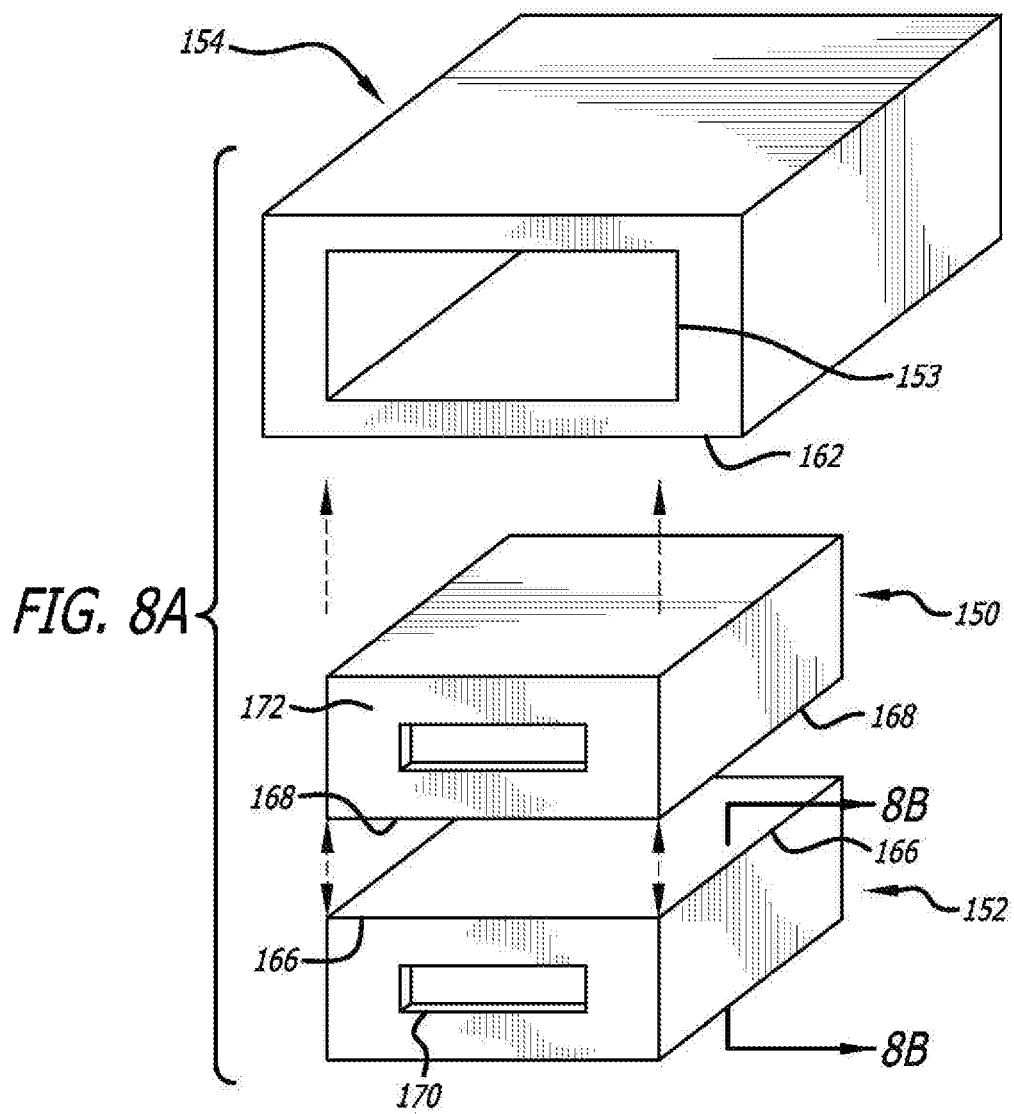
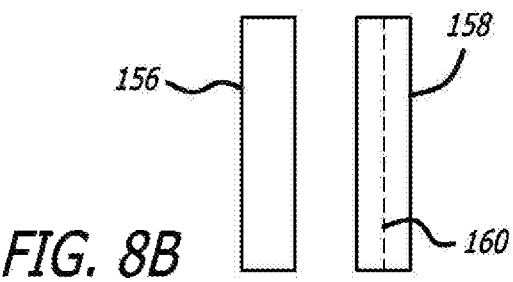

MODULAR MEDICAL ARTICLE STORAGE CONTAINER WITH TORTUOUS PATH SEAL

CROSS-REFERENCE TO RELATED APPLICATIONS

This application is a continuation of Ser. No. 16/174,208 filed Oct. 29, 2018, now U.S. Pat. No. 10,609,845, which is a continuation of U.S. application Ser. No. 15/394,788 filed Dec. 29, 2016, now U.S. Pat. No. 10,117,365, and claims the benefit of U.S. provisional Application No. 62/273,421 filed Dec. 30, 2015, the disclosures of all of which are incorporated by reference in their entireties.

BACKGROUND

The invention relates generally to a container formed of a non-electrically-conducting substrate having an electrically-conductive component so that the container has an RF shield to attenuate RF energy in the container from leaking out of the container, and more particularly, to an RF shield that includes a tortuous path seal.

As a general summary, in the field of medication administration containers are used to store medications before administration to a patient. In RFID tracking systems of today, the medications include an attached RFID tag that responds to RFID interrogation energy. When taking an inventory of a container in which RFID-tagged medications are stored, it is important that the RF activation energy transmitted by an RFID reader to the container stay within the container. Otherwise, medications that have RFID tags located outside the container may be activated by the transmitted RF energy and are read by the RFID reader. The results would therefore be inaccurate for an inventory of the container because the reader would record that the medications outside the container are inside the container when they actually are not. Shielding the container so that RF energy transmitted into the container is attenuated by the container's RF shield that it cannot activate an RFID tag outside the container is desired to avoid this problem.

Medication dispensing systems have been in use for many years. The initial purpose of such systems was to reduce medication errors associated with manual distribution and the high cost of maintaining a large amount of inventory. Current systems present many advantages, including lower costs associated with pharmaceutical distribution, improved inventory control, substance control, automated documentation, further reduction of errors, and relieving professional pharmacists and nursing personnel of many tasks.

In large medical facilities, the main inventories of pharmaceutical items are held in storage locations which are often far removed from the patients who use them. To facilitate secure and accurate delivery of the pharmaceutical items from these storage locations to the patient, a variety of systems have been proposed and put into use. In earlier systems referred to as "cart exchange" systems, medication carts are distributed at nursing stations in the medical facility, remote from the central pharmacy, and are periodically exchanged with fully supplied carts. Typically, these carts contain a twenty-four hour supply of medications sorted by patient into specific drawers. The "used" cart is returned to a central pharmacy supply area where the next twenty-four hours of medications are replenished. Narcotics are stored in locked boxes on the floor, requiring two nurses with separate keys and a written log.

Radio-frequency identification ("RFID") is the use of electromagnetic energy ("EM energy") to stimulate a responsive device known as an RFID "tag" or transponder to identify itself and in some cases, provide additionally stored data. RFID tags typically include a semiconductor device having a memory, circuitry, and one or more conductive traces that form an antenna. Typically, RFID tags act as transponders, providing information stored in the semiconductor device memory in response to an RF interrogation signal received from a reader, also referred to as an interrogator.

RFID tags may be incorporated into or attached to articles to be tracked. In some cases, the tag may be attached to the outside of an article with adhesive, tape, or other means and in other cases, the tag may be inserted within the article, such as being included in the packaging, located within the container of the article, or sewn into a garment. The RFID tags are manufactured with a unique identification number which is typically a simple serial number of a few bytes with a check digit attached. This identification number is incorporated into the tag during manufacture. The user cannot alter this serial/identification number and manufacturers guarantee that each serial number is used only once. This configuration represents the low cost end of the technology in that the RFID tag is read-only and it responds to an interrogation signal only with its identification number. Typically, the tag continuously responds with its identification number. Data transmission to the tag is not possible. These tags are very low cost and are produced in enormous quantities.

Such read-only RFID tags typically are permanently attached to an article to be tracked and, once attached, the serial number of the tag is associated with its host article in a computer data base. For example, a particular type of medicine may be contained in hundreds or thousands of small vials. Upon manufacture, or receipt of the vials at a health care institution, an RFID tag is attached to each vial. Each vial with its permanently attached RFID tag will be checked into the data base of the health care institution upon receipt. The RFID identification number is associated in the data base with the type of medicine, size of the dose in the vial, and perhaps other information such as the expiration date of the medicine. Thereafter, when the RFID tag of a vial is interrogated and its identification number read, a processor will compare the identification number to the data base of the health care institution to match that identification number with its stored data about the contents of the vial. The contents of the vial can then be determined as well as any other characteristics that have been stored in the data base. In this system, the institution maintains a comprehensive data base regarding the articles in inventory rather than incorporating such data into each RFID tag separately.

An object of the RFID tag is to associate it with an article throughout the article's life in a particular facility, such as a manufacturing facility, a transport vehicle, a health care facility, a storage area, or other, so that the article may be located, identified, and tracked, as it is moved. For example, knowing where certain medical articles reside at all times in a health care facility can greatly facilitate locating needed medical supplies when emergencies arise. Similarly, tracking the articles through the facility can assist in generating more efficient dispensing and inventory control systems as well as improving work flow in a facility. Additionally, expiration dates can be monitored electronically and those articles that are older and about to expire can be moved to the front of the line for immediate dispensing. This results in better inventory control and lowered costs.

Other RFID tags are writable and information about the article to which the RFID tag is attached can be programmed into the individual tag. While this can provide a distinct advantage when a facility's computer servers are unavailable, such tags cost more, depending on the size of the memory in the tag. Programming each one of the tags with information contained in the article to which they are attached involves further time and expense.

RFID tags may be applied to containers or articles to be tracked by the manufacturer, the receiving party, or others. In some cases where a manufacturer applies the tags to the product, the manufacturer will also supply a respective data base file that links the identification number of each of the tags to the contents of each respective article. That manufacturer supplied data base can be distributed to the customer in the form of a file that may easily be imported into the customer's overall data base thereby saving the customer from the expense of creating the data base.

Many RFID tags used today are passive in that they do not have a battery or other autonomous power supply and instead, must rely on the interrogating energy provided by an RFID reader to provide power to activate the tag. Passive RFID tags require an electromagnetic field of energy of a certain frequency range and certain minimum intensity in order to achieve activation of the tag and transmission of its stored data. Another choice is an active RFID tag; however, such tags require an accompanying battery to provide power to activate the tag, thus increasing the expense of the tag and making them undesirable for use in a large number of applications.

Depending on the requirements of the RFID tag application, such as the physical size of the articles to be identified, their location, and the ability to reach them easily, tags may need to be read from a short distance or a long distance by an RFID reader. Such distances may vary from a few centimeters to ten or more meters. Additionally, in the U.S. and in other countries, the frequency range within which such tags are permitted to operate is limited. As an example, lower frequency bands, such as 125 KHz and 13.56 MHz, may be used for RFID tags in some applications. At this frequency range, the electromagnetic energy is less affected by liquids and other dielectric materials, but suffers from the limitation of a short interrogating distance. At higher frequency bands where RFID use is permitted, such as 915 MHz and 2.4 GHz, the RFID tags can be interrogated at longer distances, but they de-tune more rapidly as the material to which the tag is attached varies. It has also been found that at these higher frequencies, closely spaced RFID tags will de-tune each other as the spacing between tags is decreased.

There are a number of common situations where the RFID tags may be located inside enclosures. Some of these enclosures may have entirely or partially metal or metallized surfaces. Examples of enclosures include metal enclosures (e.g., shipping containers), partial metal enclosures (e.g., vehicles such as airplanes, buses, trains, and ships that have a housing made from a combination of metal and other materials), and non-metal enclosures (e.g., warehouses and buildings made of wood). Examples of objects with RFID tags that may be located in these enclosures include loose articles, packaged articles, parcels inside warehouses, inventory items inside buildings, various goods inside retail stores, and various portable items (e.g., passenger identification cards and tickets, baggage, cargo, individual life-saving equipment such as life jackets and masks) inside vehicles, etc.

The read range (i.e., the range of the interrogation and/or response signals) of RFID tags is limited. For example, some types of passive RFID tags have a maximum range of about twelve meters, which may be attained only in ideal free space conditions with favorable antenna orientation. In a more realistic situation, the observed RFID tag range is often six meters or less. Therefore, some of the enclosures described above may have dimensions that far exceed the read range of an individual RFID tag. Unless the RFID reader can be placed in close proximity to a target RFID tag in such an enclosure, the tag will not be activated and read. Additionally, metal surfaces of the enclosures present a serious obstacle for the RF signals that need to be exchanged between RFID readers and RFID tags, making RFID tags located behind those metal surfaces difficult or impossible to detect.

In addition to the above, the detection range of the RFID systems is typically limited by signal strength to short ranges, frequently less than about thirty centimeters for 13.56 MHz systems. Therefore, portable reader units may need to be moved past a group of tagged items in order to detect all the tagged items, particularly where the tagged items are stored in a space significantly greater than the detection range of a stationary or fixed single reader antenna. Alternately, a large reader antenna with sufficient power and range to detect a larger number of tagged items may be used. However, such an antenna may be unwieldy and may increase the range of the radiated power beyond allowable limits. Furthermore, these reader antennae are often located in stores or other locations where space is at a premium and it is expensive and inconvenient to use such large reader antennae. In another possible solution, multiple small antennae may be used but such a configuration may be awkward to set up when space is at a premium and when wiring is preferred or required to be hidden.

In the case of medical supplies and devices, it is desirable to develop accurate tracking, inventory control systems, and dispensing systems so that RFID tagged devices and articles may be located quickly should the need arise, and may be identified for other purposes, such as expiration dates. In the case of medical supply or dispensing cabinets used in a health care facility, a large number of medical devices and articles are located closely together, such as in a plurality of drawers. Cabinets such as these are typically made of metal, which can make the use of an external RFID system for identification of the stored articles difficult. In some cases, such cabinets are locked due to the presence of narcotics or other medical articles or apparatus within them that are subject to a high theft rate. Thus, manual identification of the cabinet contents is difficult due to the need to control access.

Providing an internal RFID system in such a cabinet can pose challenges. Where internal articles can have random placement within the cabinet, the RFID system must be such that there are no "dead zones" that the RFID system is unable to reach. In general, dead zones are areas in which the level of coupling between an RFID reader antenna and an RFID tag is not adequate for the system to perform a successful read of the tag. The existence of such dead zones may be caused by orientations in which the tag and the reader antennae are in orthogonal planes. Thus, articles placed in dead zones may not be detected thereby resulting in inaccurate tracking of tagged articles.

Often in the medical field, there is a need to read a large number of tags attached to articles in such an enclosure, and as mentioned above, such enclosures have limited access due to security reasons. The physical dimension of the enclosure may need to vary to accommodate a large number of articles or articles of different sizes and shapes. In order to obtain an accurate identification and count of such closely-located medical articles or devices, a robust electromagnetic energy field must be provided at the appropriate frequency within the enclosure to surround all such stored articles and devices to be sure that their tags are all activated and read. Such medical devices may have the RFID tags attached to the outside of their containers and may be stored in various orientations with the RFID tag (and associated antenna) pointed upwards, sideways, downward, or at some other angle in a random pattern.

It is a goal of many health care facilities to keep the use of EM energy to a minimum, or at least contained. The use of high-power readers to locate and extract data from RFID tags is generally undesirable in health care facilities, although it may be acceptable in warehouses that are sparsely populated with workers, or in aircraft cargo holds. Radiating a broad beam of EM energy at a large area, where that EM energy may stray into adjacent, more sensitive areas, is undesirable. Efficiency in operating a reader to obtain the needed identification information from tags is an objective. In many cases where RFID tags are read, hand-held readers are used. Such readers transmit a relatively wide beam of energy to reach all RFID tags in a particular location. While the end result of activating each tag and reading it may be accomplished, the transmission of the energy is not controlled except by the aim of the user. Additionally, this is a manual system that will require the services of one or more individuals, which can also be undesirable in facilities where staff is limited. In many such systems, the RFID reader is a portable unit with a "tethered reader head" thereby imposing the extra time and effort to find the unit, be sure it is powered, take it to the medication cabinet where the inventory is required, open the cabinet, collect the inventory data, and then upload the inventory data to a pharmacy server. All of the foregoing can take significant amounts of time.

A problem often arises where only the RFID tags attached to medical articles located in a particular location or container are to be read for inventory purposes. For example, a tray of medical articles may exist with each of the articles in the tray having an attached RFID tag. Where the articles in the tray must be checked for possible expiration, it is common to activate the RFID tags in the tray by directing an RFID reader's beam at the tray. This will activate the RFID tag on each of the medical articles in the tray. The activated RFID tags will transmit their individual identification numbers which are received by the RFID reader. Those received identifications are communicated from the RFID reader to a processor that accesses a database to compare each received identification number to a medical article in the database to determine if any are expired.

While this system works well, problems arise when the activating RFID beam was strong enough to reach the RFID tags on medical articles that are stored in the locality of the tray but are not in the tray. The tags of these remote articles will also be activated, they will transmit their identification data, and the RFID reader will read their identifications, not knowing that those medical articles are not in the tray. If one of those medical articles having an activated tag that is located outside the tray is determined to be expired, inaccuracy and time wasting can result. Even though the tray itself does not have any expired articles in it, it will probably be removed from use because the reading process identified an expired article. Then each medical article in the tray will now likely need to be visually inspected to determine if it is expired. The item that was reported expired will not be found in the tray but the tray is unavailable for use until this discrepancy has been found.

Consequently, manufacturers of RFID tracking systems strive to furnish an electrical isolation container also called an RF shielded container, within which the tray is placed before it is scanned. The RF shielded container is sometimes referred to as a Faraday cage and its six metallic and electrically connected walls greatly attenuate the passage of electrical energy into and out of the container. The RFID reader antenna(s) is placed inside the RF shielded container. However, the radiated signal will leak out of gaps, slots, openings, and other discontinuities that may be present in the RF shielded container. These leaked signals are free to radiate in open space and may cause the activation of remote RFID tags. Conversely, signals can travel into the RF shielded container in the same manner.

For RFID reading energy having higher frequencies, good shielding effectiveness can usually be achieved by the use of thin metal shielding as the container material or lining, but the assumption is that the shield is continuous and fully surrounds the RFID-tagged articles without gaps or apertures. However, it has been found that gaps or apertures and other openings can be very difficult to avoid. Seams needed for manufacturing, doors, drawers, and other openings made for various purposes penetrate the shielded container, which can lower the shielding performance of the container. Welding, brazing, or soldering is used to make seams between sheets that are permanently secured. The metal faces to be joined must be clean to promote complete filling of the seam with conductive metal. Screws or rivets are less satisfactory methods to secure the seams because permanent low-impedance contact along the seams between the fasteners is difficult to maintain with these methods. A total lack of contact along any part of the seam results in a thin gap capable of acting as a slot antenna. Such an antenna transmits energy at wavelengths shorter than about four times the gap length.

Radio frequency ("RF") activation energy transmitted within the walls of a Faraday cage container is greatly attenuated at the walls and very little if any energy will leak from that container. As a result only the RFID tags in the isolation container are read. This can then solve the problem of inadvertently reading remote RFID tags that are not in the container; however, making and distributing RF shielded containers have associated problems, some of which have been described above.

In medical applications, current systems used for tracking items with RFID technology consist of heavy, sometimes custom made, and more expensive, metal containers. These metal containers are basic in design due to the cost and difficulty of shaping metal into aesthetically pleasing shapes. These containers consist of sheet metal that has been bent into shape and then welded to form an enclosure. The enclosures are fabricated by hand and therefore are expensive. The sheet metal enclosures are also relatively heavy and therefore require expensive hardware for stacking multiple units or to mount under cabinets, desks, and work stations. The design of the enclosures is that of a basic six-sided enclosure and even when painted appear simple and plain with no design features. In addition, the thermal conductivity of the metal is high compared to plastic or other electrically non-conductive materials making it difficult to insulate these enclosures for cold storage applications.

When such metal enclosures include a drawer or multiple drawers, the weight of the enclosure is even higher. Heavy metal administration or storage cabinets can be difficult to move and place in desired positions and present an even more difficult handling situation when they are required to be stacked on one another.

RFID tracking containers are needed for various storage uses and the sizes required of the containers for such uses are different. A requirement to manufacture different sizes of RFID tracking containers, one for each possible use, can be very expensive and inefficient. Similarly, having to use a shielded container that is much too large for the particular application at hand is inefficient and can be expensive. It would be preferred if a modular approach to assembling an RF shielded container were available. In such a modular approach, various modules of different sizes and configurations would be available, all of which may physically fit together in various configurations as needed, and the RF shielding arrangements of these modules would be designed to fit together to result in a fully RF shielded container for operating an RF tracking system within the container.

Hence, those of skill in the art have recognized a need for modular RF-shielded containers that may be assembled together to form various container shapes and sizes thereby obviating the expense of creating custom containers. Another need has been recognized by those of skill in the art for reducing the cost of medical item containers and reducing their weight. Yet a further need has been recognized for using a less expensive material to build such containers, yet providing such containers so that they nevertheless are RF shielded. Those of skill in the art have also recognized a need for a more reliable configuration of the walls of a container so that when assembled to provide the container, a better RF shield of the container is produced. The invention fulfills these needs and others.

SUMMARY OF THE INVENTION

The invention is directed to a lightweight, low cost, RF-shielded, and aesthetically pleasing alternative to the prior art metal enclosures described above. The invention provides a system of modular RF-shielded plastic components that can be paired in various combinations to create RF-shielded drawers, containers, and enclosures of differing heights for the purpose of tracking items of differing heights. Configurations provide both Faraday cages and tortuous path seals for preventing RF leakage.

In one aspect there is provided a medical article storage container having an internal storage space, the storage container being shielded from leaking radio-frequency ("RF") energy out of and into the storage space, the container formed with a plurality of interconnected walls, the container comprising a first wall located at a side of the storage space, the first wall comprising a substrate formed of an electrically non-conductive material, the first wall having a joining edge configured to physically mate with another wall to form a joint seam between the two walls, the first wall also comprising an electrically conductive component that is configured to be coextensive with the first wall substrate and extend to the joining edge of the first wall substrate at which location the electrically conductive component is exposed to electrically connect with an electrically conductive component of another wall at the joint seam, the first wall also comprising a portion of a channel extending outwardly at the joining edge, the channel portion being as wide as the joining edge and having a shape including a bend and configured to physically mate with a complementary portion of a channel of another wall that is joined with the first wall at the joint seam, and a second wall located at a side of the storage space, the second wall comprising a substrate that is formed of an electrically non-conductive material, the second wall having a joining edge that is physically mated with the joining edge of the first wall to form a joint seam between the two walls, the second wall also comprising an electrically conductive component that is configured to be coextensive with the second wall substrate and extend to the joining edge of the second wall substrate at which location the electrically conductive component is exposed, the electrically conductive component of the second wall being electrically connected to the electrically conductive component of the first wall at the joint seam, the second wall also comprising a portion of a channel extending outwardly at the joining edge of the second wall, the channel portion of the second wall being as wide as the joining edge of the second wall and having a complementary shape to the shape of the portion of the channel of the first wall including the bend, the second wall channel portion being physically mated with the channel portion of the first wall to form an electrical channel with a bend thereby providing a tortuous path seal at the joint seam to attenuate RF energy leaking out of and into the storage space, whereby the electrical connections of the first and second walls form a part of a Faraday cage around the storage space and the tortuous path seal provides additional shielding against RF leakage.

In more detailed aspects, the electrically conductive components of both the first and second walls are embedded into their respective walls and are configured to extend beyond the joining edges of their respective walls and be exposed to electrically mate with an electrically conductive component of another wall at the joint seam thereby shielding the storage space from leaking RF energy. In another aspect, the electrically conductive components of both the first and second walls are embedded into their respective walls so that they form an outer surface of the wall and are configured to contact an electrically conductive component of another wall at the joint seam thereby shielding the storage space from leaking RF energy. In yet a further aspect, the electrically conductive components of both the first and second walls are disposed over an outer surface of their respective walls and are configured to contact an electrically conductive component of another wall at the joint seam thereby shielding the storage space from leaking RF energy.

Other aspects include the channel forming a tortuous path seal by the first and second walls comprises a tortuous path having two bends thereby increasing attenuation of energy RF energy out of an into the storage space. In one case, the bend of the tortuous path seal is an angle of ninety degrees.

In yet a further aspect, the electrically-conductive component of the first wall comprises an electrically conductive metallic mesh embedded in the first wall substrate, the mesh having openings of a size selected in accordance with the frequency of the RF energy operating in the storage space to provide a predetermined amount of attenuation of that RF frequency energy at the first wall.

In other aspects, the first and second walls of the storage container have selectable sizes relative to each other wherein the first wall is used in a first storage container of a first size and the second wall is used in a second storage container of a second size that is different from the first storage container, wherein the first and second storage containers are modular containers that are connected together at joint seams of the first walls of the first storage container being connected to the second walls of the second storage container. A joint seam at which two modular containers are connected together comprises a rib comprising an RF energy channel having a bend thereby providing a tortuous path seal that attenuates RF energy leaking out of and into the storage space formed by the interconnection of the modular containers.

In another aspect, the channel is configured with a size that attenuates RF energy that is used for operation in the storage space, the channel further comprising electrically conductive shielding foam located at the bend in the channel, the electrically conductive shielding foam configured to attenuate RF energy in the channel, thereby providing an electrical shield for the storage space. The channel further comprises electrically conductive adhesive applied to the foam at a selected position in the channel, the electrically conductive adhesive holding the foam permanently in the selected position and contributing to the electrical shield of the storage space. The channel is configured with a size that attenuates RF energy that is used for operation in the storage space, the channel further comprising metal wool shielding located within the channel, the metal wool configured to attenuate RF energy in the channel, thereby providing an electrical shield for the storage space.

A further aspect is the substrates of the first and second walls are formed of a plastic having a relatively low coefficient of electrical conductivity whereby a lighter wall is provided.

In yet more detailed aspects, the first wall comprises an opening providing access to the internal storage space, the first wall also comprising a door attached to an outer surface of the first wall mounted for covering the opening at one position and uncovering the opening in a second position, the door comprising electrically conductive material on its inner surface coextensive with the size of the door to electrically mate with the electrical component of the first wall to provide an electric shield at and across the opening of the first wall, the first wall further comprising a portion of a tortuous path seal located about the opening of the first wall, and the door comprising a second portion of a tortuous path of a complementary shape to that of the portion on the wall configured to accept the portion of the tortuous path of the door when the door is in the closed position such that the tortuous path is completed when the door is in the closed position, whereby both a portion of a Faraday cage is provided by the electrical contact of the door with the electrical component of the opening and a tortuous path seal if provided by the portions of the torturous seal being formed when the door is in the closed position.

Further, the tortuous path seal has a size selected to attenuate energy at an operating frequency in the storage space, and includes further shielding through the use of electrical shield foam held in place with an electrically conductive adhesive at the bend.

In another aspect, the medical article storage container further comprises a drawer slidably located in the opening of the first wall and movable into and out of the storage space, the drawer comprising the door over the opening by having a front wall that is larger than the opening in the first wall of the container and is located outside the medical article storage container but is movable to a closed position in relation to the medical article container at which the front wall of the drawer moves into contact with the first wall and covers the opening, wherein the drawer is formed of an electrically nonconductive material, wherein the drawer front wall includes an electrically conductive component coexistent with the front wall of the drawer and configured at the front wall of the drawer so that when the drawer is in the closed position, the electrically conductive component of the front wall of the drawer is placed into physical and electrical contact with the electrically conductive component of the first wall at the opening of the drawer, wherein the front wall of the drawer further includes a portion of a tortuous path located about the edges of the front wall, and wherein the first wall of the medical article container includes a second portion of a tortuous path located about the opening in the first wall and having a shape that is complementary to the tortuous path portion disposed about the edge of the front wall of the drawer configured so that when the drawer is closed, the two portions of the tortuous path mate and form a tortuous path seal shielding the storage space from leakage into and out of the storage space of electrical energy.

In a more detailed aspect, the tortuous path located about the front wall of the drawer has a bend configured to attenuate electrical energy.

In yet a further detailed aspect, the medical article storage container further comprises a first module having a false bottom under which are located an RFID reader and RFID probe and antenna, and comprising a second module containing the internal storage space coupled to the first module, the RFID reader and RFID probe and antenna configured to be usable with different sizes of second module attached to the first module of the container. The second module is attached to the first module at a joint seam, the container further comprising an RFID shielding rib located over the joint seam and providing a Faraday cage shield and a tortuous path seal at the joint seam.

In accordance with method aspects of the invention, there is provided a method of shielding an internal storage space of a medical article storage container from RF energy leakage out of and into the internal storage space, comprising surrounding the internal storage space with a plurality of walls, the walls having a plastic substrate with an embedded electrically conductive component that is coextensive with the substrate, connecting together the coextensive electrically conductive components of adjacent walls at joint seams, wherein each wall has a joining edge configured to mate physically and electrically with a joining edge of another wall to form a joint seam, thereby providing electrically conducting walls located completely around the internal storage space operating as a Faraday cage to attenuate RF energy and shield the internal storage area from leakage of RF energy, and forming an RF tortuous path seal at each joint seam through connecting together a first portion of an RF tortuous path located at a first wall at the joint seam with a complementary portion of an RF tortuous path located at a second wall at the same joint seam as the first and second walls are mated together, wherein connecting together the first and complementary portions of the RF tortuous path provides a complete RF tortuous path configured to attenuate RF energy, thereby forming a Faraday cage around the entire internal storage area and forming tortuous path seals at the joint seams of the walls when connecting the walls together, whereby the internal storage area is shielded against the leakage of RF energy out of the internal storage area and RF energy into the storage area by both a Faraday cage and tortuous path seals.

The features and advantages of the invention will be more readily understood from the following detailed description of embodiments that should be read in conjunction with the accompanying drawings.

BRIEF DESCRIPTION OF THE DRAWINGS

FIGS. 8A and 8B depict an exploded perspective view of a top plastic container and a bottom plastic container for insertion into an RF-enabled enclosure or drawer;

DETAILED DESCRIPTION OF PREFERRED EMBODIMENTS

Detailed embodiments of the present invention are disclosed herein; however, it is to be understood that the disclosed embodiments are merely exemplary and the invention may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to employ the present invention.

Figure 1:
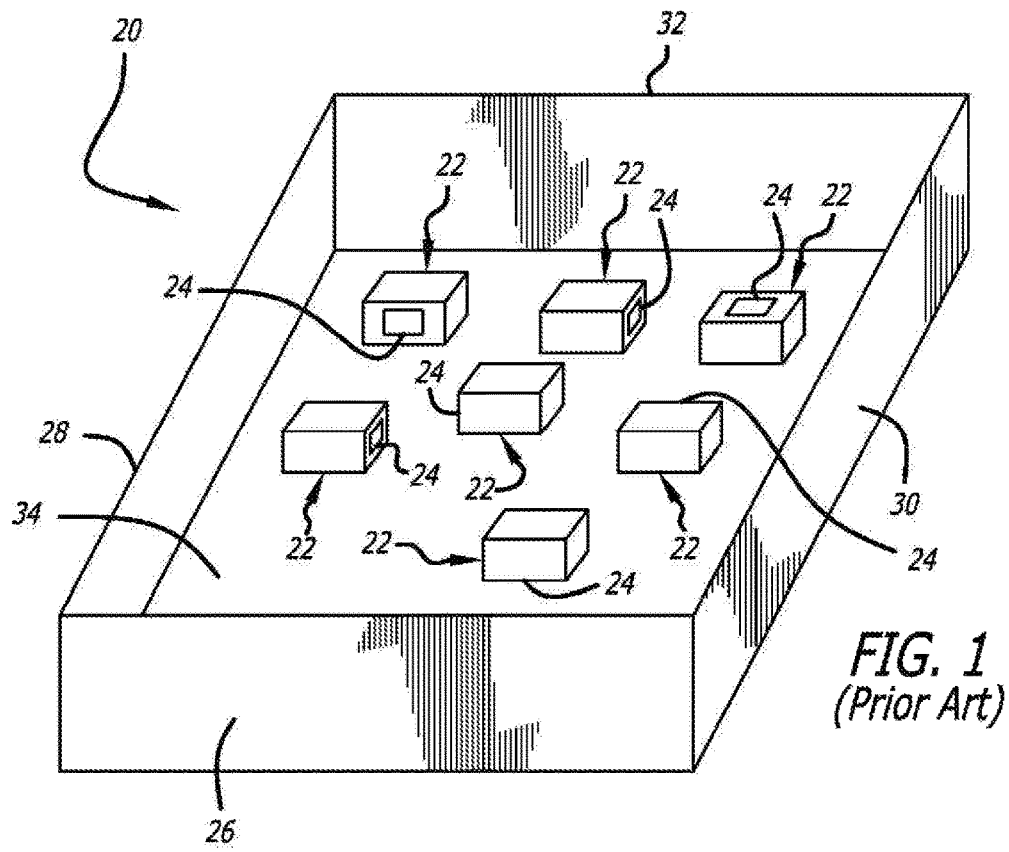
FIG. 1 is a schematic diagram of a prior art drawer that may be positioned within a medical dispensing cabinet, showing the storage of a plurality of medical articles randomly positioned in the drawer, each of those articles having an integral RFID tag with the articles, and therefore the tags on them, oriented randomly in the drawer.

Referring now in more detail to the exemplary drawings for purposes of illustrating embodiments of the invention, wherein like reference numerals designate corresponding or like elements among the several views, there is shown in FIG. 1 a schematic representation of a prior art device including a partial enclosure 20 in which a plurality of medical articles 22 are stored, each with a respective RFID tag 24 that has a unique identification number. The partial enclosure may comprise a drawer having a front wall 26, a left side wall 28, a right side wall 30, a rear wall 32, and a bottom 34. These articles are randomly distributed in the drawer with the RFID tags facing in various and random directions.

As used in regard to the embodiments herein, "tag" is meant to refer to an RFID transponder. Such tags are well known and typically have a coupling element, such as an antenna, and an electronic microchip. The microchip includes data storage, also referred to as memory.

Figure 2:
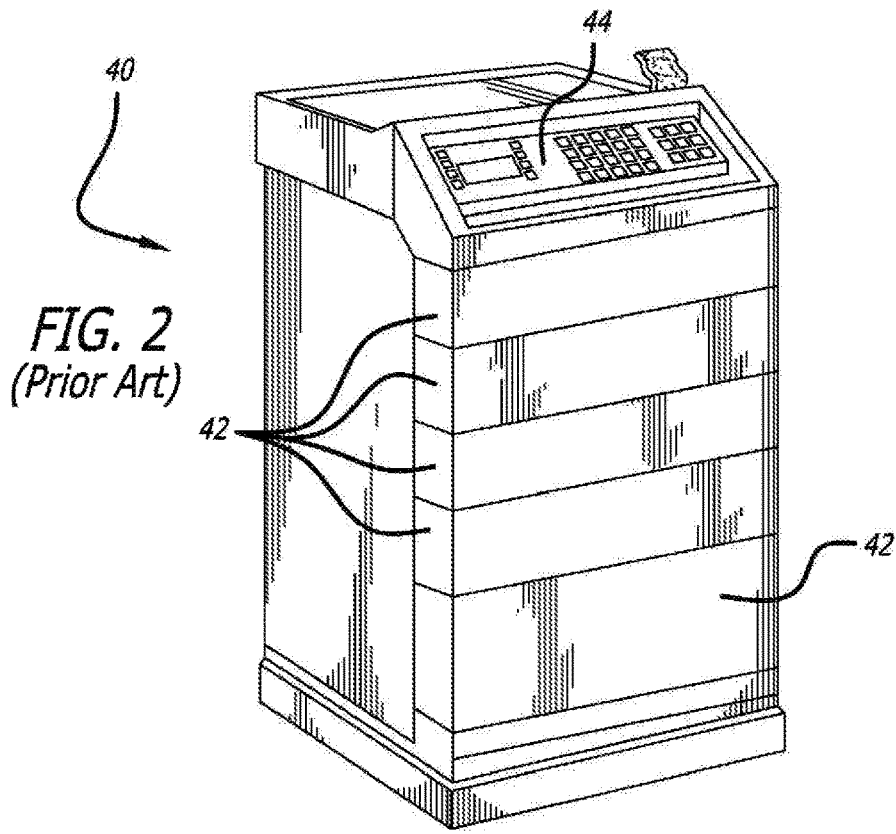
FIG. 2 is a perspective view of a prior art medication dispensing cabinet ("ADC") having five drawers, one of which is similar to the schematic view of FIG. 1, the cabinet also having an integral computer for controlling access to the cabinet and for performing inventory tracking by periodically reading RFID tags placed on articles stored within the cabinet to identify stored medical articles, and for reporting the identified articles to a remote computer.

FIG. 2 depicts a representative prior art medical dispensing cabinet 40 comprising a plurality of movable drawers 42. In this embodiment, there are five drawers that slide outwardly from the cabinet so that access is provided to the contents of the drawers. FIG. 1 is a schematic diagram of a representative drawer that may be positioned within the cabinet of FIG. 2 for sliding outward to provide access to the drawer's contents and for sliding inward into the cabinet to secure the drawer's contents. The cabinet also comprises an integral computer 44 that may be used to control access to the drawers and to generate data concerning access and contents of the drawers, and to communicate with other systems. In this embodiment, the integral computer 44 includes a non-volatile memory device (not shown), such as a server, and generates data concerning the number and type of articles that are identified in the drawers through an RFID tracking system. The integral computer 44 stores a database on the memory device that correlates RFID tag identification numbers with medical articles identified in the drawers. The database in one embodiment includes the names of the patients for whom the identified medical articles in the drawers have been prescribed, the prescribed medications, their prescribed administration dates and times, their expiration dates (if any), the health care practitioner who prescribed the medical article, as well as other information.

In a simpler system, the integral computer 44 may simply receive the unique identification numbers from the RFID tags on the stored medical articles and pass those identification numbers to an inventory control computer that has access to a database for matching the RFID tag identification numbers to medical article descriptions.

Such a cabinet 40 may be located at a nursing station on a particular floor of a health care institution and may contain the prescriptions for the patients of that floor. As prescriptions are prepared for the patients of that floor, they are delivered and placed into the cabinet 40. They are logged into the integral computer 44, which may notify the pharmacy of their receipt. A drawer may also contain non-prescription medical supplies or articles for dispensing to the patients as determined by the nursing staff. At the appropriate time, a nurse would access the drawer in which the medical articles are stored through the use of the computer 44, remove a particular patient's prescriptions and any needed non-prescription articles, and then close the drawer so that it is secured. In order to access the cabinet, the nurse may need to provide various information and may need a secure access code. The drawers 42 may be locked or unlocked as conditions require.

Figure 3:
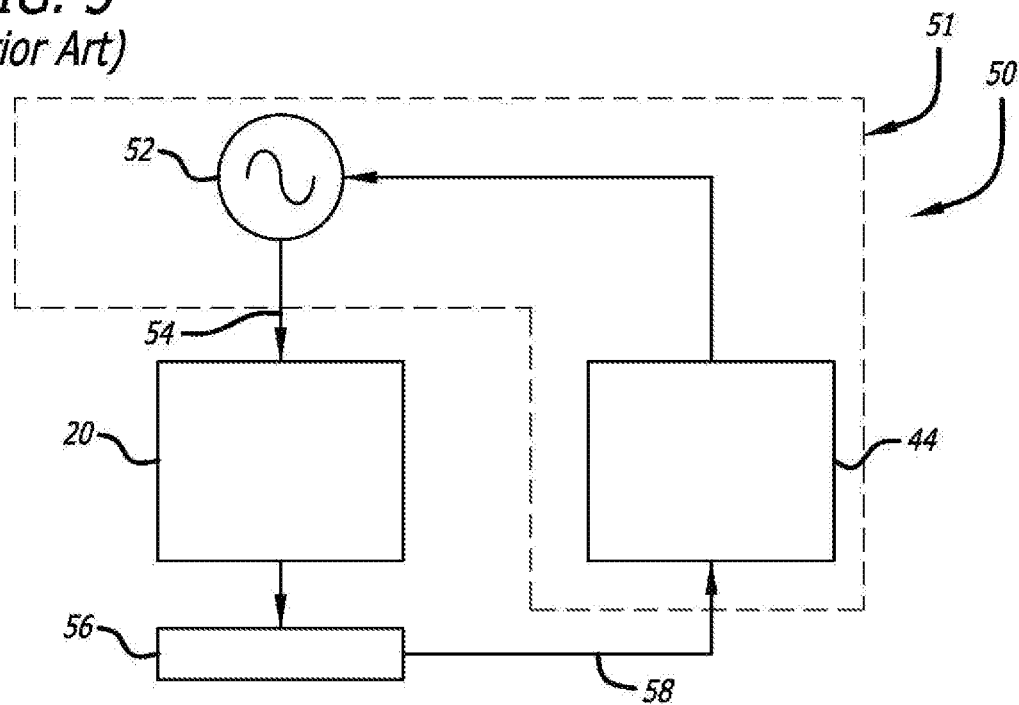
FIG. 3 is a block and flow diagram showing an embodiment in which an RFID reader transmits activating electromagnetic ("EM") energy into a drawer containing RFID tags with a single transmitting antenna, receives the data output from the activated RFID tags with a single receiving antenna, a computer controlling the transmission of activating energy, and receiving the data from the activated RFID tags for processing.
Figure 4:
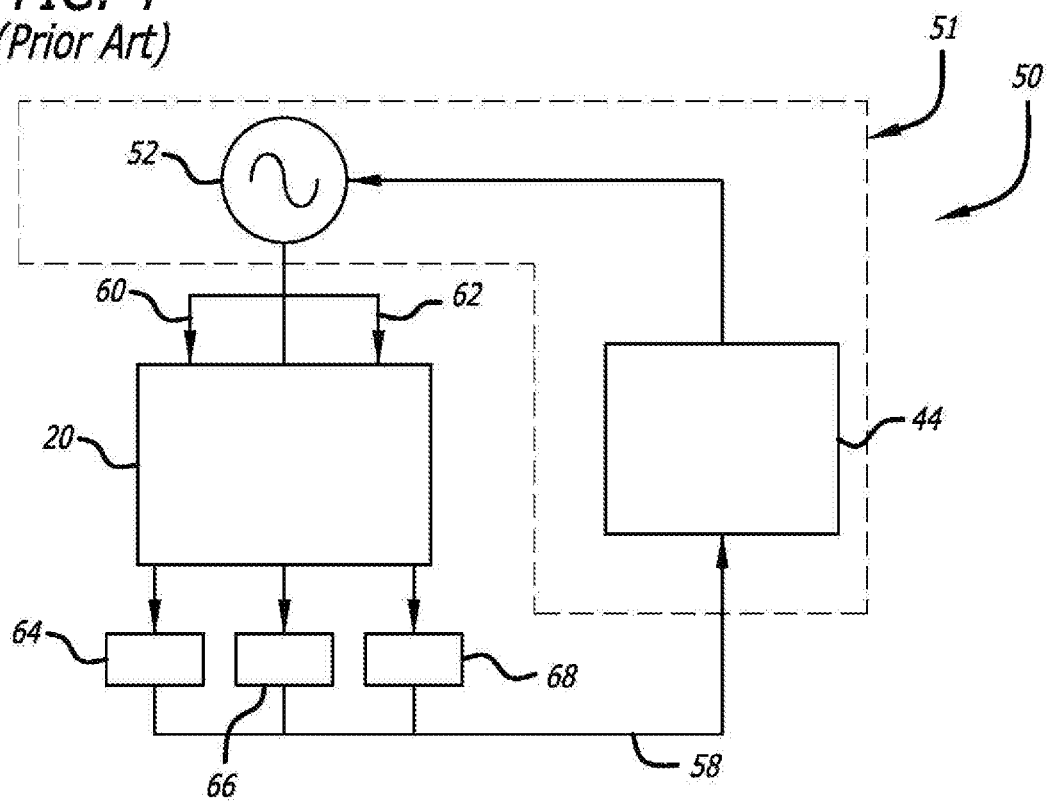
FIG. 4 is block and flow diagram similar to FIG. 3 showing an embodiment in which an RFID reader transmits activating EM energy into a drawer containing RFID tags with two transmitting antennae, receives the data output from the activated RFID tags with three receiving antennae, and as in FIG. 3, a computer controlling the transmission of activating energy and receiving the data from the activated RFID tags for processing.

Systems that use RFID tags often employ an RFID reader in communication with one or more host computing systems that act as depositories to store, process, and share data collected by the RFID reader. Turning now to FIGS. 3 and 4, a prior art system and method 50 for tracking articles are shown in which a drawer 20 of the cabinet 40 of FIG. 2 is monitored to obtain data from RFID tags disposed with articles in that drawer. As mentioned above, a robust field of EM energy needs to be established in the storage site so that the RFID tags mounted to the various stored articles will be activated, regardless of their orientation.

In FIGS. 3 and 4, the prior art tracking system 50 is shown for identifying articles in an enclosure and comprises a transmitter 52 of EM energy as part of an RFID reader. The transmitter 52 has a particular frequency, such as 915 MHz, for transmitting EM energy into a drawer 20 by means of a transmitting probe 54. The transmitter 52 is configured to transmit the necessary RFID EM energy and any necessary timing pulses and data into the enclosure 20 in which the RFID tags are disposed. In this case, the enclosure is a drawer 20. The computer 44 of an RFID reader 51 controls the EM transmitter 52 to cycle between a transmit period and a non-transmit, or off, period. During the transmit period, the transmitted EM energy at or above a threshold intensity level surrounds the RFID tags in the drawer thereby activating them. The transmitter 52 is then switched to the off period during which the RFID tags respond with their respective stored data.

The embodiment of FIG. 3 comprises a single transmitting probe 54 and a single receiving antenna 56 oriented in such a manner so as to optimally read the data transmitted by the activated RFID tags located inside the drawer 20. The single receiving antenna 56 is communicatively coupled to the computer 44 of the reader 50 located on the outside of the drawer 20 or on the inner bottom of the drawer. Other mounting locations are possible. Coaxial cables 58 or other suitable signal links can be used to couple the receiving antenna 56 to the computer 44. A wireless link may be used in a different embodiment. Although not shown in the figures, those skilled in the art will recognize that various additional circuits and devices are used to separate the digital data from the RF energy, for use by the computer. Such circuits and devices have not been shown in FIGS. 3 and 4 to avoid unneeded complexity in the drawing.

The prior art device of FIG. 4 is similar to the prior art device of FIG. 3 but instead uses two transmitting probes 60 and 62 and three receiving antennae 64, 66, and 68. The configuration and the number of transmitting probes and receiving antennae to be used for a system may vary based at least in part on the size of the enclosure 20, the frequency of operation, the relationship between the operation frequency and the natural resonance frequency of the enclosure, and the expected number of RFID tags to be placed in it, so that all of the RFID tags inside the enclosure can be reliably activated and read. The location and number of RFID reader components can be dependent on the particular application. For example, fewer components may be required for enclosures having a relatively small size, while additional components, such as shown in FIG. 4, may be needed for larger enclosures. Although shown in block form in FIGS. 3 and 4, it should be recognized that each receiving antenna 56, 64, 66, and 68 of the system 50 may comprise a sub-array in a different embodiment.

Figure 5:
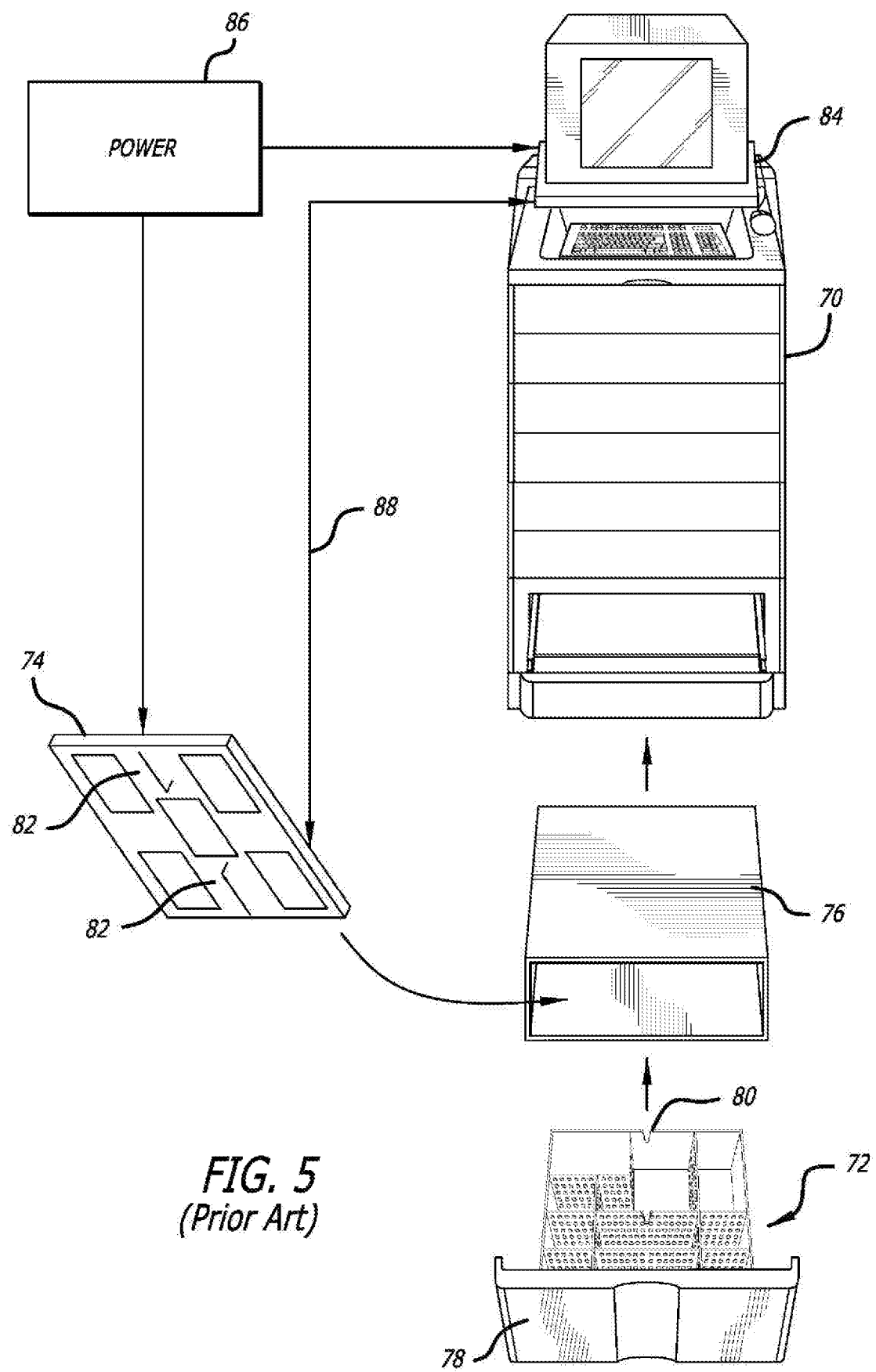
FIG. 5 is an exploded view of a prior art ADC with the lower drawer removed and the frame of the cabinet visible in the cavity where the drawer was located, showing a representation of a Faraday cage to be formed within the frame at the cavity for the removed drawer, an RFID-enabling module, to be mounted within the cavity so that at least the antennae are within the Faraday cage, and the drawer having partitions to be slidably mounted within the representation of the Faraday cage, and also showing power and data connections for the module with the ADC.

In FIG. 5 there is shown a medication cabinet 70 having its bottom drawer 72 removed. In this case, the bottom drawer is formed of plastic and does not provide a Faraday cage for use in RFID-enabling the drawer. Also shown is an "RFID-enabling" drawer module 74 designed to establish and provide an environment in the removed drawer 72 in which items having RFID tags placed in the drawer can be detected, identified, and tracked. The module in this embodiment includes probes and receiving antennae that must be mounted within a Faraday cage formed by or formed around the drawer 72. Because the RFID-enabling module disclosed herein can generate a robust EM field in a container regardless of the resonant frequency of that container, retrofitting a drawer such as shown in FIG. 5 becomes possible. The robust EM field created by the RFID-enabling module system is able to activate all RFID tags within the drawer so that they may be read and the item to which they are attached can be identified and tracked.

Because the present drawer 72 is formed of plastic, a Faraday cage must be formed around it. Accordingly, a Faraday cage, represented schematically in FIG. 5 as a box 76, is formed around the drawer. In the embodiment shown, it may comprise metallic walls that are mounted within the frame of the cabinet 70 to completely enclose the drawer once is it reinserted into the cabinet and closed. The metallic walls may be formed by various ways, one of which is to install metallic foil in the frame about the drawer. The foil should be large enough to engage the front 78 wall of the drawer to thereby complete the Faraday cage around the storage area 104 of the drawer. The drawer front wall may also be painted with metallic paint on the outside, sides, and inside the front panel to make contact with the foil in the frame of the cabinet and complete a Faraday cage that includes the front wall of the drawer. As another embodiment, metallic paint may be used within the frame of the cabinet to create the Faraday cage. Other means may also be used to construct or complete the Faraday cage to surround the container in which items are being identified and tracked.

In an embodiment where the drawer is metallic and itself forms a Faraday cage, the antennae of the module 74 must be mounted to be within the cage to communicate with the field and RFID transmissions within the cage. In some cases, the module is placed above the drawer and in other cases, it may be placed below the drawer, depending on the configuration of the cabinet and the drawer. Additionally more than one drawer in a cabinet can be RFID-enabled, according to aspects of the invention.

As mentioned, the module 74 can be mounted above the drawer to RFID-enable the drawer. In the embodiment shown in FIG. 5, the module has two probes 82 that protrude above its surface by a certain distance. In this case, they are centered on the module. To accommodate those antennae, a notch 80 has been formed in the back of the drawer so that the drawer back will not damage the probe antennae when the drawer is pulled to the open position and pushed to the closed position. The module 74 may be mounted within the Faraday cage by standoffs and screws into the ceiling of the frame around the drawer. Other mounting techniques are possible.

FIG. 5 also shows connection of the module 74 to a power source 86 and to data communications 88 with a local computer 84. In the embodiment where the module 74 is connected to an Ethernet (not shown), the power may be provided entirely by the Ethernet connection (Power over Ethernet or "PoE"). Additionally, the local computer 84 may be programmed to process RFID data of identified and tracked items by the module 74 in the RFID-enabled drawers 72 of the cabinet 70, and may also be programmed to create a data base of those items and the RFID data associated with them. The processed RFID data and the data base may be communicated to a central server and its data base, or may be communicated elsewhere or to additional locations. The local computer 84 would also contain a data base of the installed hardware, the hardware address correlated to which drawer, and other various data base items. Since construction of such a program and data base are well within the skill of those in the art, no further detail is provided here.

Figure 6A:
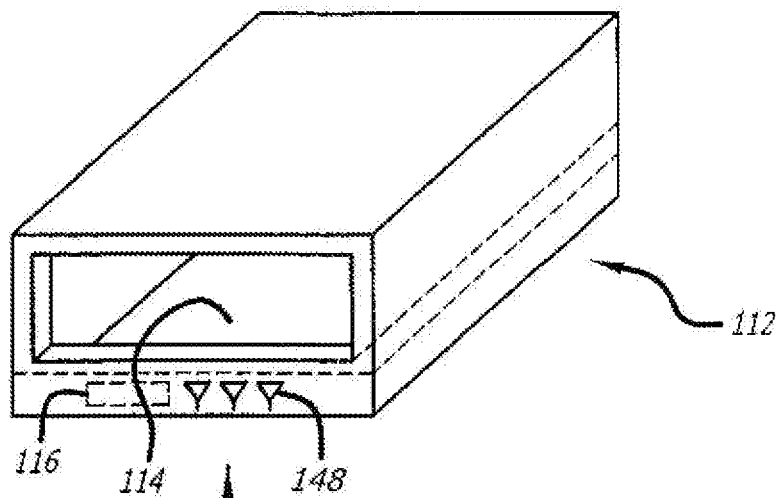
FIG. 6A is a perspective front view of a container, also referred to as an enclosure, having an opening in which a slidable drawer may be mounted, the enclosure having a false bottom in which an RFID reader circuit and an associated antenna or antennae are mounted.
Figure 6B:
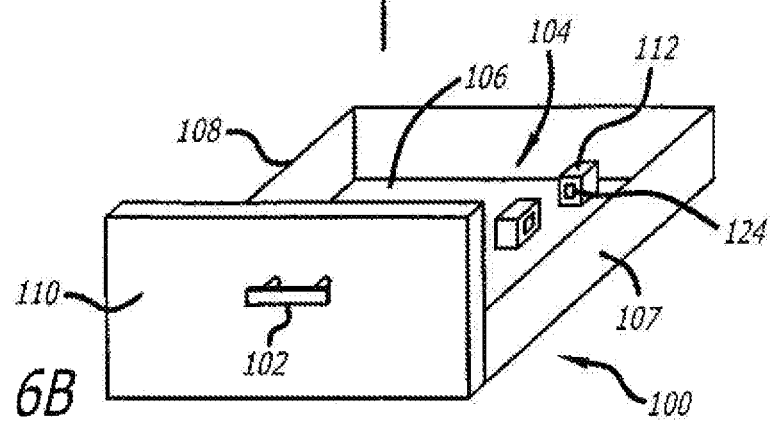
FIG. 6B presents a view of a drawer for use in the container of FIG. 6A, the drawer having front wall with a handle that are rigidly mounted to the side walls of the drawer.

In keeping with the invention, and referring to FIGS. 6A and 6B, an RF-enabled drawer 100 is used to identify and track medical articles with an RFID tag system. The drawer 100 functions similarly to a standard mechanical drawer in that a handle 102 or knob is used to open the drawer revealing the storage area 104. In this embodiment, the drawer bottom 106, left side 108, right side 107, and back side 109 are fabricated from a non-metallic material that is transparent to RF energy, such as a plastic. The drawer front wall or door 110 is formed from a metallic or RF-shielded material in order to form the RF-shielded front door of the drawer enclosure 112 and complete a Faraday cage around the storage area of the drawer.

The drawer enclosure 112 (FIG. 6A), which is formed of a metallic material, includes a false bottom 114 in which the RFID reader 116 and antennas 148 are mounted, and above which the storage area 104 of the drawer 100 slides. The RFID tags 124 attached to the items 122 (e.g., medical articles) stored in the drawer are identified by the modulated RF energy transmitted by the antennas 148 mounted in the false bottom 114. The area under the false bottom, which exists to protect the RFID reader and antennas, and the area surrounding the drawer storage area 104, together make up the RF-enabled enclosure. In this embodiment, the drawer enclosure 112 is formed of a metallic material, and together with the door 110, form a Faraday cage around the storage area of the drawer. In other words, the drawer enclosure 112 can be formed from a metallic material, while the drawer 100 itself is formed from a non-metallic material that is transparent to RF energy, except for the front wall. The front wall of the drawer, the door 110, is formed of a metallic or RF-shielded material in order to complete the Faraday cage.

Figure 6C:
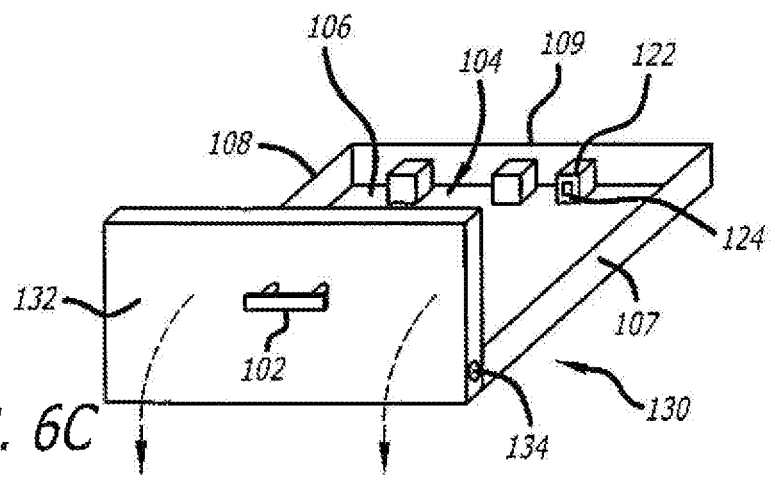
FIG. 6C presents a drawer similar to FIG. 6B except that the front wall of the drawer is hingedly mounted to the side walls, both of FIGS. 6B and 6C showing medical articles located in the drawers, each article having an RFID tag attached.

In another embodiment shown in FIG. 6C, another embodiment of an RF-enabled drawer 130 is shown for use in tracking medical articles in its storage area 104 and is similar to the RF-enabled drawer 100 of FIG. 6B. The difference is that the front wall comprises a hinged door 132 that is formed of a metallic material and attached to the storage area 104. The hinged door 132 opens downward, or upward, on a hinge 134, or sideways on one hinge, or two doors opening opposite one another on hinges (i.e., French doors). The door 132 is formed of a metallic or RF-shielded material and it forms the front cover of the drawer enclosure 130 as shown in FIG. 6C.

Figure 7A:
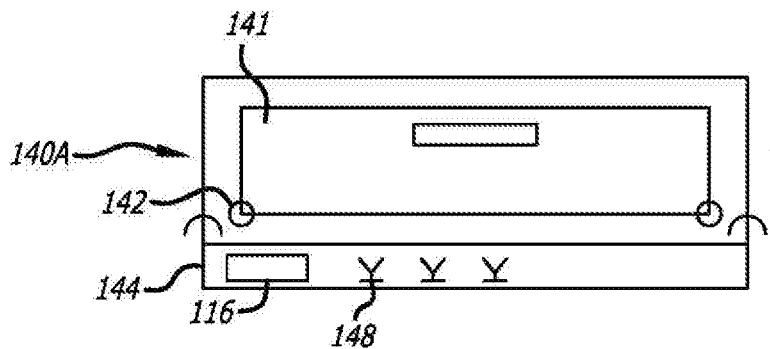
FIGS. 7A, 7B, and 7C are schematic diagrams that depict the use of modular containers of plastic components of different sizes with a standard base having a false bottom with an RFID reader and an antenna or antennae for reading RFID tags, with FIG. 7A having the smallest size of an upper drawer module, FIG. 7B having a middle size of an upper drawer module, and FIG. 7C having the largest size of an upper drawer module, with FIG. 7D presenting an example schematic diagram of a drawer storing a medical article that has an RFID tag attached.
Figure 7B:
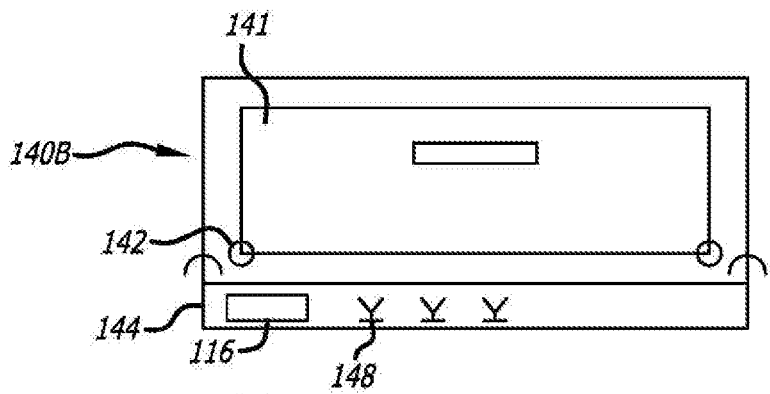
Figure 7C:
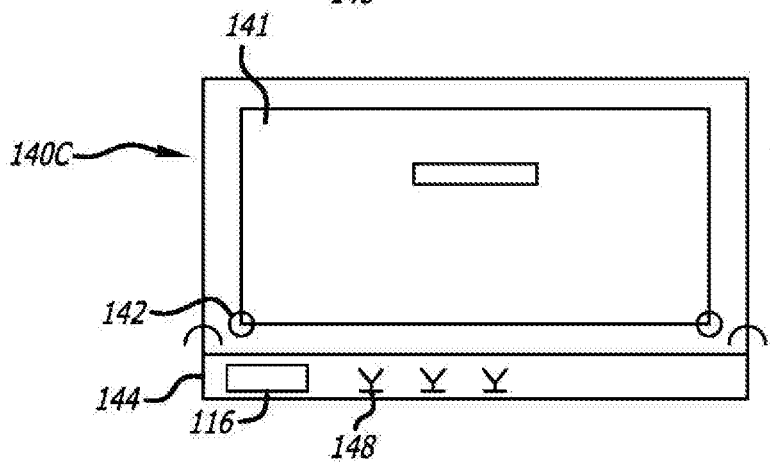

In another embodiment, as shown in the schematic front view diagrams of FIGS. 7A, 7B, and 7C, RF-enabled enclosures 140A, 140B, and 140C are used to track medical articles. These enclosures comprise the same modular lower container 144 that includes a false bottom in which is located an RFID reader 116 and probes and antennas 148, as required. However, the upper modular containers in these figures are different sizes. In particular, FIG. 7A has the smallest upper modular container, FIG. 7B has a middle size upper modular container, and FIG. 7C has the largest upper modular container. In one embodiment, the height of the drawer in FIG. 7A was two inches (5.08 cm), the height of the drawer in FIG. 7B was three inches (7.62 cm), and the height of the drawer in FIG. 7C was four inches (10.16 cm).

Figure 7D:
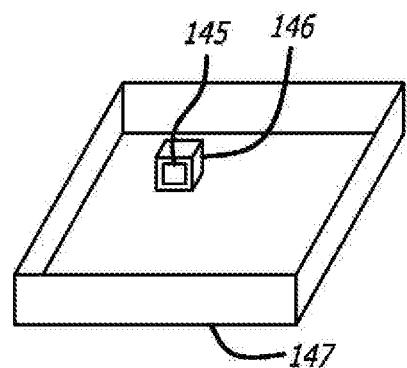

In each case of FIGS. 7A, 7B, and 7C, the enclosure is accessed by way of a door 141 that opens downward or upward on a hinge 142 or sideways on one hinge or two doors opening opposite one another on hinges (i.e., French doors). Opening the door of this enclosure reveals a space or volume into which non-metallic trays 147 (FIG. 7D), bins, boxes, etc., can be placed for identification of the RFID tagged 145 items 146 contained therein. The hinges are shown schematically in the figures by circles at the lower left and right corners of the doors, for illustration only. The coupling location of the upper module 140A to the lower module 144 in FIG. 7A, for example, is schematically shown by semi-circles with the open portion of the semi-circle facing downward. This schematic indicator is also used for illustration purposes only and it not indicative of or restricted to any particular joint type or connecting mechanism.

The enclosures shown in FIGS. 7A, 7B, and 7C all include a false bottom 144 which is of the same height as the false bottom 114 in the RF-enabled drawer enclosure 112 of FIG. 6A. The RFID tags attached to medical articles, such as RFID tag 145 attached to medical article 146, stored in trays 147, bins, boxes, etc., located within the upper modular containers are identified by the modulated RF energy transmitted by antennas 148 mounted in the false bottom 144. The area under the false bottom, which exists to protect the reader and antennas, and the area in which the trays, bins, boxes, etc., are placed, together make up the RF-enabled enclosure. In this embodiment, the false bottom 144 is identical in size for each top portion of the RF-enabled enclosure 140A, 140B, and 140C. The height of the enclosures 140A, 140B, and 140C differ in order to accommodate different sized items 146 placed in the trays, boxes, bins 147. The interface between the enclosures 140A, 140B, 140C and the false bottom 144 is designed to incorporate tortuous path features as described below. All of these RF-enabled components together help to form a Faraday cage.

In one embodiment, as shown in FIG. 8A, a top plastic container 150 and a bottom plastic container 152 form an enclosure when paired together. The top and bottom containers 150, 152, are stacked together for insertion through opening 153 and placement inside of an RF-enabled (shielded) drawer 154.

The RF-shielded plastic bottom container 152 is formed of an inner shell 156 and an outer shell 158 formed of a plastic material. As shown in FIG. 8B, the outer shell 158 is RF-shielded by incorporating a metal screen or metal mesh 160 onto or into the plastic during the forming process. The inner shell 156 is not shielded, and is composed of an RF transparent material such as plastic, and serves as the false bottom 162 of the RF-enabled drawer 154. The plastic bottom container 152 also includes shielded torturous path features, around the top perimeter 166 for attachment to the top plastic container 150. The plastic bottom container 152 of the drawer enclosure also includes an opening or cut out 170 in the front of the component to provide drawer access.

The plastic top container 150 of the RF-shielded plastic drawer enclosure 154 in FIG. 8A can be a single or double shell plastic component and includes at least one shell that is RF-shielded during the forming process such as shown in FIG. 8B. The plastic top container 150 also includes shielded torturous path features (not shown), around the bottom perimeter 168 for attachment to the plastic bottom container 152. The plastic top container 150 includes an opening or cut out 172 in the front of the component to provide drawer access.

Both top and bottom RF-shielded plastic containers 150 and 152 include features around the perimeter of the opening or cut out 170 and 172 that facilitate the RF sealing of a drawer face plate (not shown) to the drawer enclosure 154. One bottom RF-shielded plastic container 152 can be fabricated to mate with several top RF-shielded plastic containers to form RF drawer enclosures of differing heights. For example, an RF-enabled automated dispensing cabinet might require three different drawer heights for storing RF-tagged items. The same bottom RF-shielded plastic container can be used for all three "different heights" top RF-shielded plastic containers. The top RF-shielded plastic container 150 defines the height of the drawer 154.

Figure 9:
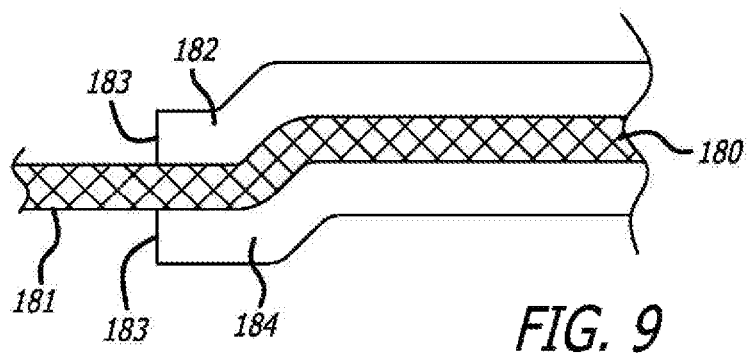
FIG. 9 depicts a partial cross-sectional view of an 80 gauge steel mesh (electrically conductive) sandwiched between an outer shell and an inner shell both of which are formed of a plastic material that is RF transparent (electrically nonconductive), thereby forming an RF shielded wall material, the diagram also showing that the steel mesh comprises a portion that extends beyond the edge created by the plastic layers and is therefore exposed.

The RF-shielded plastic components described above are formed by a process whereby the RF-shielding material is incorporated onto or into the plastic during the forming process. In one embodiment, as shown in FIG. 9, the shielding material is an 80 gauge steel mesh 180 that is attached to the surface of either or both of an outer shell 182 and an inner shell 184. In one embodiment, the 80 gauge metal mesh is attached with adhesive between the inner and outer shells, i.e., sandwiched between the plastic shells to form a shielding wall for use in a Faraday cage. Alternatively, a conductive epoxy can be used to attach and sandwich the metal mesh 180 between the outer and inner shells 182, 184. In this embodiment, the mesh 180 is coextensive with the plastic layers (outer and inner shells 182 and 184) and has a portion 181 that extends beyond the edge 183 formed by the plastic layers. As is shown in other figures below, this extended portion is used to make connection with electrically conductive components of other walls or features of other plastic devices.

As is used herein, coextensive means that the electrically conductive mesh, or layer, or paint, or other material has a size that is at least as large as the plastic component into which or on which it is embedded. Its purpose is to provide a Faraday cage around the storage area formed by plastic walls. In the case of FIG. 9, the metal mesh 180 is not only coextensive with the plastic shells, it is larger than the shells so that it can be manipulated into electrical contact with the electrically conductive material of other walls, drawers, doors, or other components of a plastic enclosure.

Different RF energy ranges will require appropriate gauge metal mesh to form the Faraday cage. For example, the metal mesh can range from 60 gauge to 120 gauge depending on the level of RF energy used with the RFID tags.

Figure 10A:
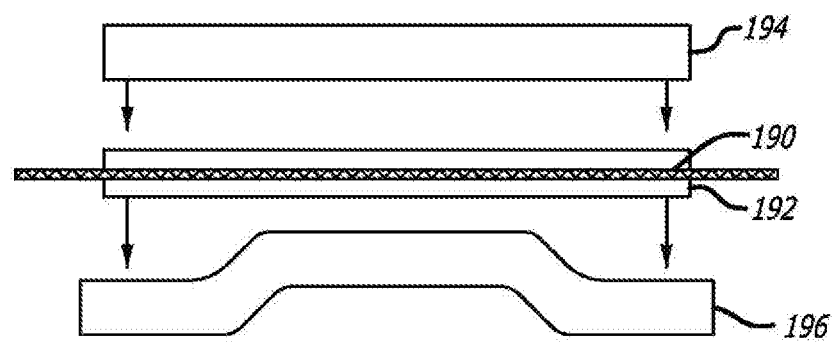
FIGS. 10A through 10C depict a forming process for embedding a metal mesh within a plastic shell by using a thermoform mold wherein a portion of the metallic mesh (electrically conductive component) extends beyond the plastic components so that it is exposed.
Figure 10B:
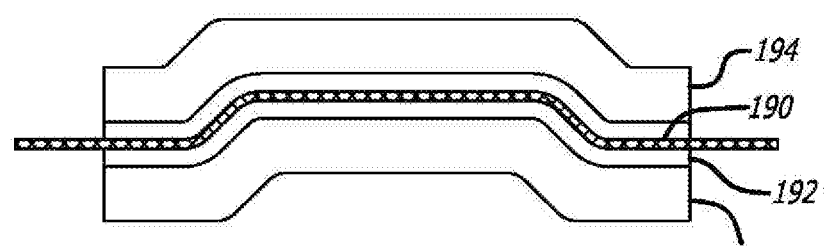
Figure 10C:
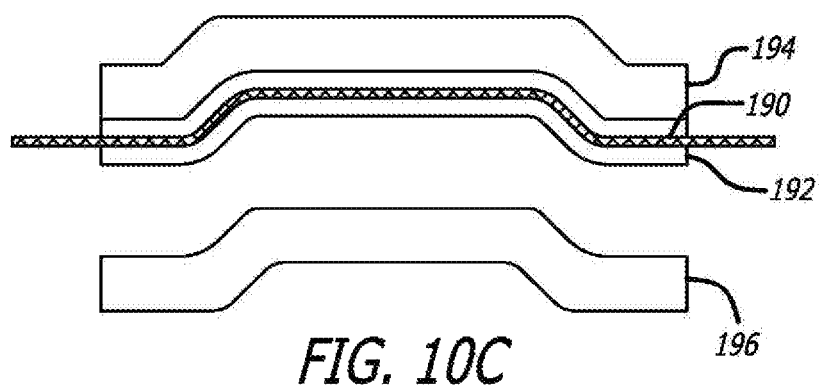

In one embodiment, as shown in FIGS. 10A through 10C, the electrically conductive metal mesh 190 is procured embedded in a polyester shell 192, or similar plastic material, and molded into the enclosure plastic. In this embodiment, the metal mesh 190 is procured or purchased with the metal mesh being embedded in the polyester (plastic shell) 192, and then the plastic shell 192 is molded along with a second plastic shell 194 by thermoforming on thermoform mold 196 as shown in FIG. 10B. In this embodiment, as in FIG. 9, the metal mesh 190 is not only coextensive with the plastic shell, but it is also longer than the shell and extends past an edge of the plastic shell for use in making electrical contact with electrically conductive material of other walls or parts of an enclosure. Further referring to FIG. 10B, the mold 196 is shown thermoforming the plastic shell 192 having an electrically-conductive mesh 190 embedded in it and the second plastic shell 194 being molded.

The end product, as shown in FIG. 10C, is the plastic shell 192 and the second plastic shell 194 taking the shape of the thermoform mold 196, with the metal mesh 190 also conforming to the thermoform mold. The embedded metal mesh 190 into plastic shell 192 results in an RF-enabled Faraday cage suitable for forming the containers, drawers, plastic boxes, plastic shells, and other plastic components described herein. In another embodiment, the metal mesh is procured embedded in polyester, or similar plastic material, and then molded separately from the enclosure plastic. Then the two molded components nest together in the final assembly of the RF-enabled enclosure.

Figure 11:
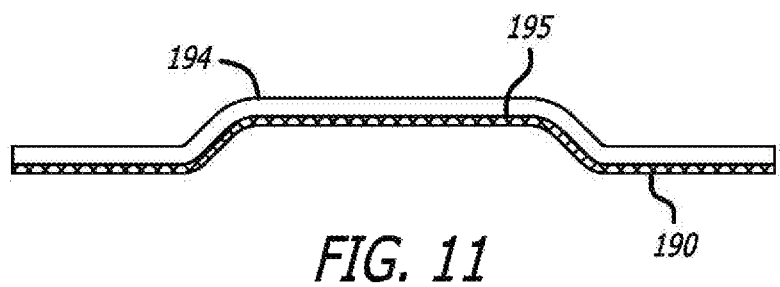
FIG. 11 depicts another formed plastic wall in which is embedded an electrically conductive component. In this embodiment, the metal component is placed into an indent that exists in the side of the plastic wall and has been heated to embed that metal mesh into place in the side of the plastic shell by using a thermoform mold. The electrically conductive metal component is therefore exposed continually.

Referring now to FIG. 11, a different type of wall is shown. In this embodiment, the plastic material 194 included an indent 195 on its underside. An electrically conductive metal mesh having a thickness equal or less than the depth of the indent was inserted into that indent. The metal mesh is held in place in the indent with adhesive, or thermoforming or by other means. Because of the depth of the indent and the equal or smaller thickness of the metal mesh, the underside of the plastic with the metal mesh is smooth.

In one embodiment of the invention, a top plastic enclosure and a bottom plastic enclosure are mated together similarly to those shown in FIG. 8A. The plastic enclosures are shielded with either an embedded metal mesh or a conductive metal coating in order to form a Faraday cage. Importantly, there is a risk of RF energy leakage at the mating surfaces where the two halves are joined together. The same risk applies to a door that mates with an opening in a container or drawer. The inventor has found that positioning a tortuous path at this position substantially reduces the risk of RF energy leaking out of the container. A tortuous path is one that is not straight but instead has at least one bends. Each bend in the tortuous path causes attenuation in RF energy traversing the path. Whether by reflections or resistance, the energy is attenuated and leakage of RF energy out of the container is reduced. In order to ensure a tortuous path seal, the mating surfaces include both foam seals at the mating surfaces and a conductive epoxy in order to reduce the likelihood of RF energy leakage. Further, in one embodiment, a plastic door is connected to either the top or bottom drawers and is hinged to open and close for access into to the drawer. The plastic door includes an embedded mesh or conductive coating in order to form a Faraday cage with the RF-shielded top and bottom plastic drawer or enclosure. In order to eliminate or reduce the likelihood of RF energy leakage through the seal existing between the door and the enclosure, a foam seal and a conductive epoxy are positioned between the door and the drawer.

Foam RF shields, also referred to as seals are available from Chomerics, 77 Dragon Street, Woburn, Mass. 018898. For example, the Soft-Shield® 4850 UL 94 V-O, multiplanar EMI gaskets and the plated fabric wrapped foam EMI shielding gaskets have been found to be useful. Certain foam shields have an adhesive mounted at one side. To use the adhesive for mounting the foam at a selected location, a removable tape strip is peeled away from the adhesive.

As disclosed herein there are numerous embodiments of RF-shielded enclosures in which there are mating surfaces that may be exposed and susceptible to RF energy leakage, thus requiring a torturous path seal. In one embodiment, a plastic enclosure is comprised of a plastic material embedded with a metal mesh or conductive metal coating as described above. A plastic door having an embedded metal mesh or conductive coating mates with and closes an opening in the RF-enabled plastic enclosure or container. In this embodiment, several foam seals are incorporated into channels and between ridges on the inner surface of the door. The door ridges and channels mate with complementary ridges and channels of the plastic enclosure. Further, in order to ensure a tortuous path door seal, a conductive epoxy is applied between the door inner surface and the ridges and channels. This will reduce the likelihood or eliminate any RF energy leakage around the mating surfaces between the door and the plastic enclosure.

Figure 12:
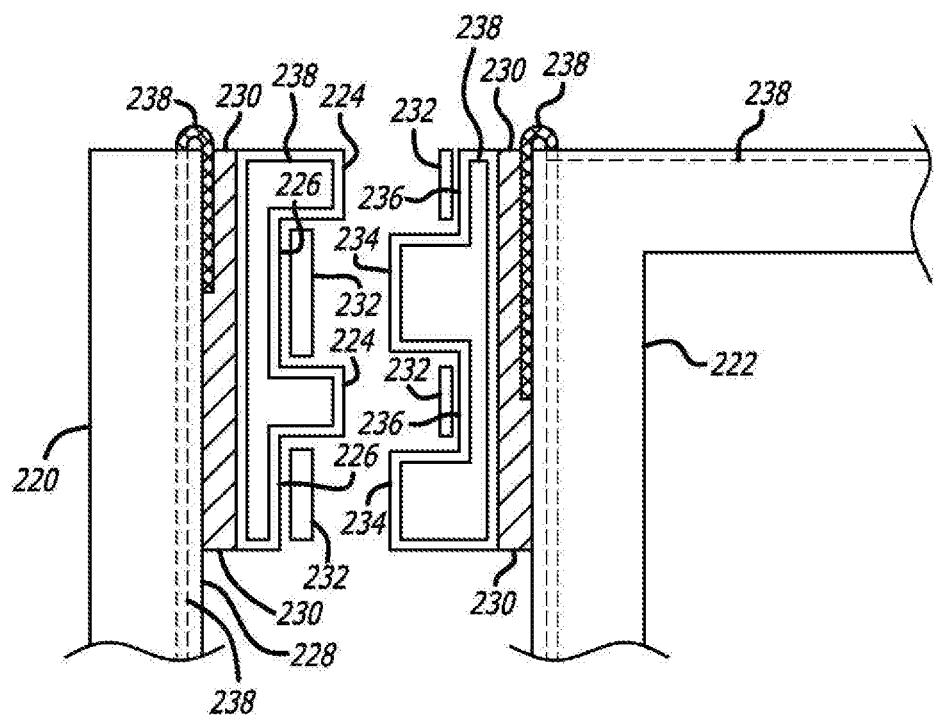
FIG. 12 depicts a partial cross-sectional view of a plastic container mating with a plastic door, each having an exposed electrically conductive component and each including mating ridges and channels for forming a tortuous path seal between the mating surfaces.

In another embodiment, as shown in FIG. 12, a tortuous path seal is formed between a plastic or metal drawer 220 and a thermoform plastic or metal container 222. In this embodiment, a thermoform RF-enabled plastic or a metal formed container 222, receives a RF-enabled plastic drawer 220, or a drawer formed from a metallic structure. Importantly, the mating surfaces between the drawer and the container require a tortuous path seal. The drawer includes ridges 224 and channels 226 on the inner surface 228 of the drawer, with a conductive epoxy 230 attaching the ridges 224 and channels 226 to the inner drawer surface 228. A foam seal 232 is positioned in the channels 226. Similarly, the container 222 includes ridges 234 and channels 236 that are matingly configured to mesh with the ridges 224 and channels 226 of the drawer 220. The ridges 224, 234 and channels 226, 236 of the drawer 220 and container 222 are attached by the conductive epoxy 230. If the drawer 220 and container 222 are formed of a plastic material, it will be embedded with a metal mesh screen 238 or coated with a conductive layer in order to form a Faraday cage.

In another embodiment, as shown in FIGS. 13A through 13D, a modular plastic RF-shielded enclosure 240 has an upper half 242 and a lower half 244 of plastic RF-shielded material joined together to form a tortuous path connection between the components. In this embodiment, both plastic sections include embedded metal mesh screens 246 or exposed screen material, or an embedded conductive metal layer, for low resistance connections between the sections, and the formation of a Faraday cage within the enclosure. Importantly, where the two halves of the plastic shielded enclosure are joined, a tortuous path seal is required in order to reduce the likelihood or eliminate RF energy leakage.

Figure 13A:
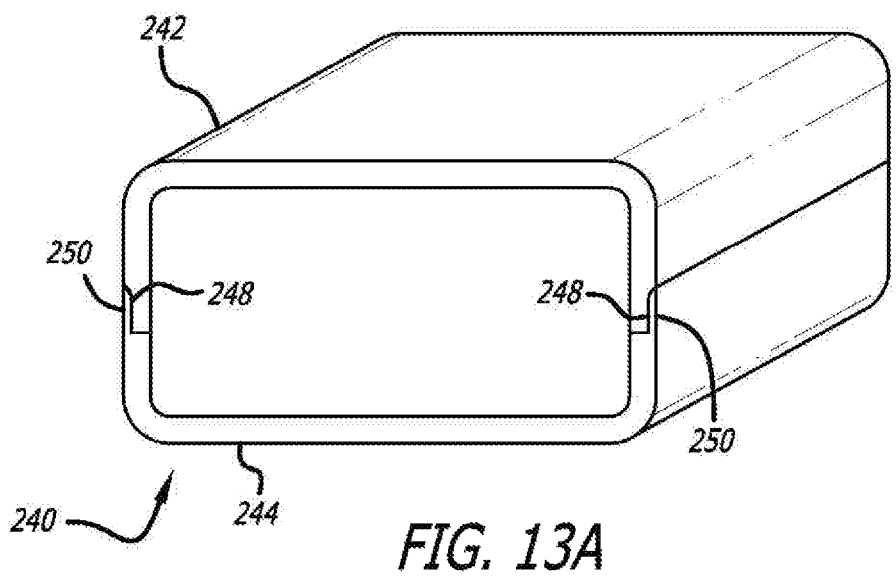
FIGS. 13A through 13D depict in schematic form and partial cross-sectional form, a top half and a bottom half of an enclosure connected together by a U-shaped inner and outer rib, the halves of the enclosure both having an embedded electrically conductive component that is coextensive with the plastic wall in which it is embedded and extends beyond the edge of the plastic wall so that the electrically conductive component is exposed, and is bent into a configuration in which it contacts the electrically conductive component of another wall to complete a Faraday cage around the enclosure.
Figure 13B:
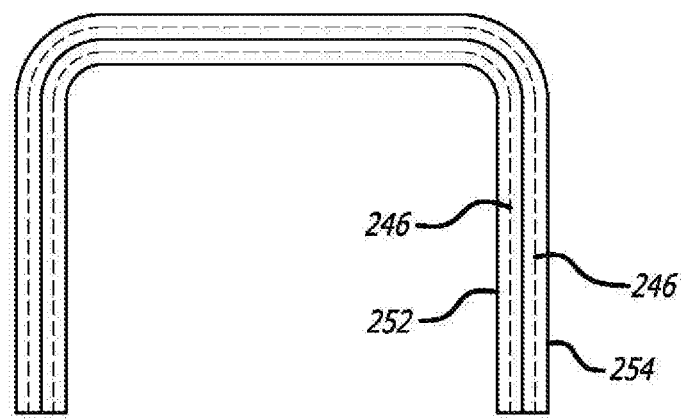
Figure 13C:
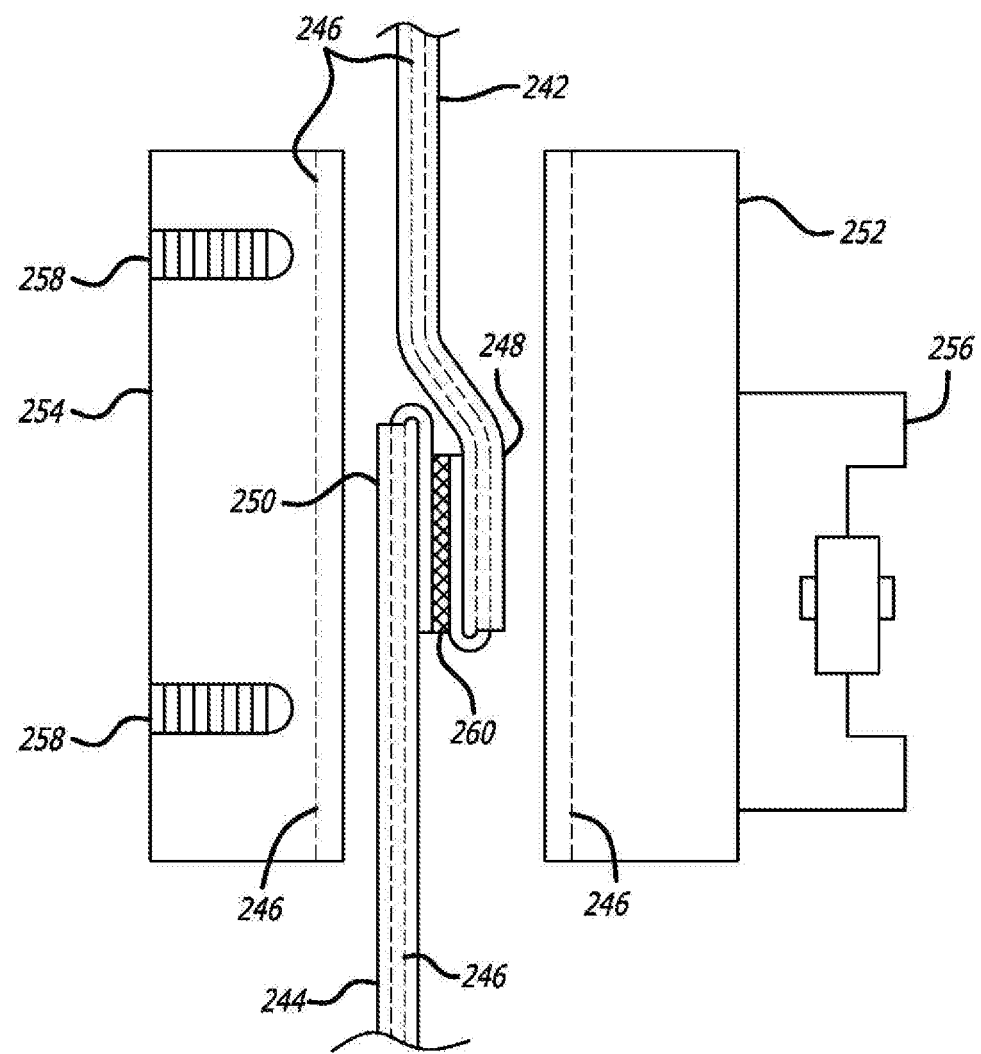
Figure 13D:
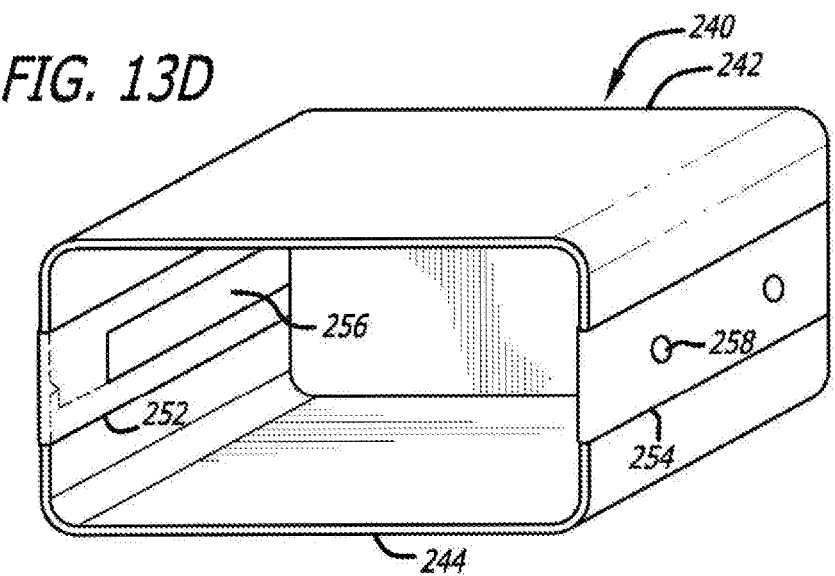

In this embodiment, the top half 242 of the plastic RF-shielded enclosure includes an offset mating surface 248 which mates with a second mating surface 250 of the lower half 244 of the RF-shielded enclosure 240. In order to connect the upper half of the enclosure to the lower half of the enclosure and to form the tortuous path seal, a U-shaped inner rib 252 is matingly attached to a U-shaped outer rib 254. The inner and outer ribs 252, 254 are formed from plastic and are RF-shielded with the embedded metal mesh screen 246. As shown in FIG. 13D, the inner and outer ribs 252, 254 connect the upper half 242 to the lower half 244 along the offset mating surface 248 and the second mating surface 250. In addition, the U-shaped inner rib 252 provides a solid base to which drawer rails 256 are mounted while the U-shaped outer rib 254 provides a base by including threaded inserts 258 to which screws can be used to attach the outer rib to a cabinet, as more clearly shown in FIG. 13C. A metal fabric or foam, or a conductive epoxy 260 is positioned between the first and second mating surfaces in order to further reduce the likelihood or eliminate RF-energy leakage at the mating surfaces. Additionally, the embedded metal mesh screens 246 of the upper and lower halves 242 and 244 have extended beyond the edge of the plastic substrates of the halves and have been bent around between the two pieces 242 and 244 to touch and create an electrical connection. Also, the electrically conductive epoxy adhesive 260 will also contribute to completing that electrical connection.

Figure 14:
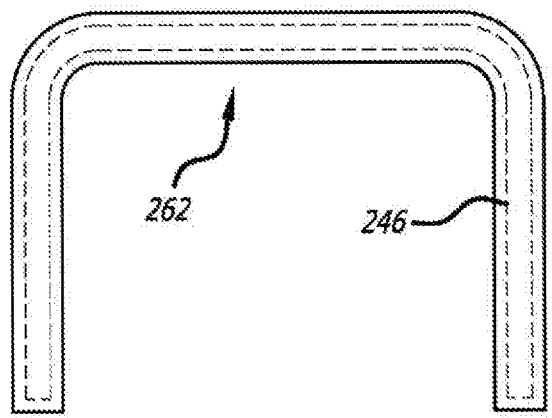
FIG. 14 depicts a partial cross-sectional view of a one-piece inner and outer rib such as that shown in FIGS. 13*b* and 13D.
Figure 15:
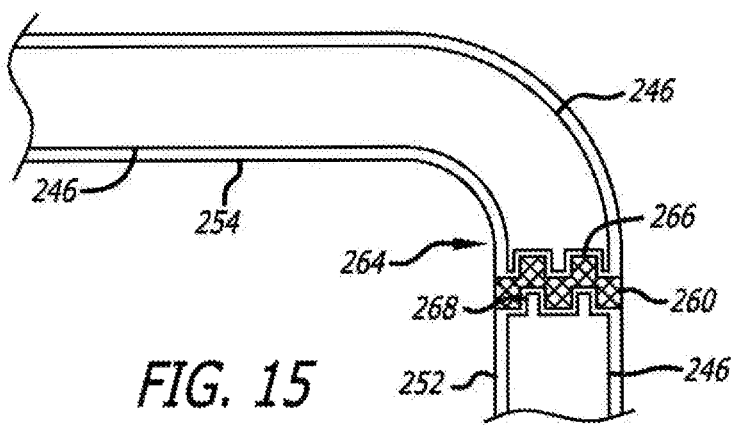
FIG. 15 depicts a partial cross-sectional view of a two-piece inner and outer rib connected together with exposed electrically conductive mesh in contact to complete a Faraday cage and having ridges and channels for establishing a tortuous path RF seal.
Figure 16:
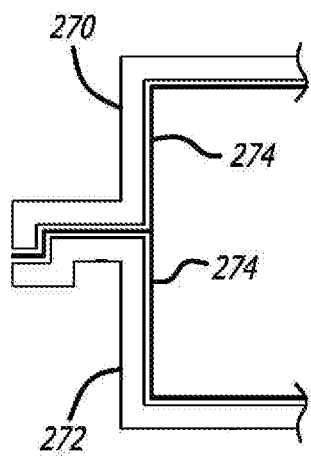
FIGS. 16 through 25 depict in schematic and partial cross-section form various embodiments of a first mating component attached to a second mating component wherein a Faraday cage is completed and a tortuous path RF seal is also formed by the particular physical and electrical mating technique. These figures also show the use of use of embedded metal mesh components in plastic walls, exposed electrically conductive components, the use of electrically conductive foam as an RF shield, the use of conductive adhesive as an RF shield, and the use of a bundle electrically conductive strands of metal wool as an RF shield.
Figure 17:
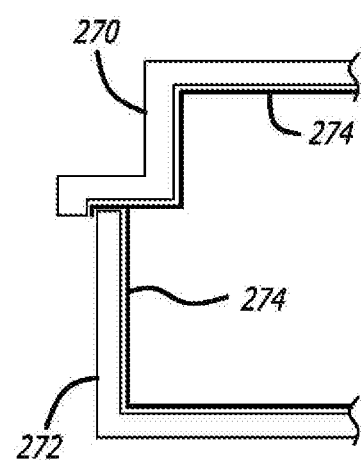
Figure 18:
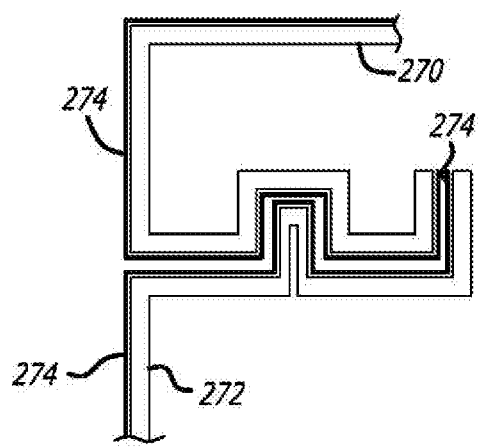
Figure 19:
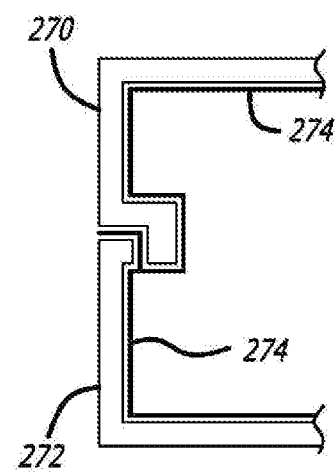

The inner and outer ribs shown in FIGS. 13A through 13D can be formed of a one-piece construction 262 as shown in FIG. 14, or a two-piece construction 264 as shown in FIG. 15. Each of the embodiments shown in FIGS. 14 and 15 include embedded metal mesh or screen or embedded conductive layers in order to form a Faraday cage, as well as reducing the likelihood or eliminating RF energy leakage by forming a tortuous path seal between mating surfaces. Either embodiment also can be coated with a conductive material. With respect to FIG. 15, the inner and outer ribs are formed of a two-piece construction. For example, the outer rib 254 is joined to the inner rib 252 by a series of mating channels 266 in the outer rib 254 and projections 268 in the inner rib with a conductive epoxy 260 used as the adhesive to join the two rib sections.

Numerous other embodiments exist for forming a tortuous path seal between multiple parts for forming an effective and operable Faraday cage from shielded plastic enclosures or components. For example, as shown in FIGS. 16-25, various enclosures, containers or drawers have mating surfaces that require a tortuous path seal between the mating surfaces to avoid RF leakage. Each embodiment includes a first mating component 270 and a second mating component 272 having surfaces that mate together where the potential for RF energy leakage can occur. In order to reduce the likelihood or eliminate RF energy leakage between the mating components 270 and 272, each of the components is embedded with a metal mesh screen 274 either entirely within the plastic of the wall or embedded so that it forms an outside wall surface. Some of the embodiments have used the metal mesh 274 that extends past the mating surface to wrap around the bends and into contact with extended external metal mesh in the opposing piece. Further, in some embodiments, a conductive epoxy 276 is positioned between the first mating component 270 and the second mating component 272. Likewise, a foam or conductive foam 278 can be placed between the first and second mating components in order to form a tortuous path seal between the mating surfaces.

Figure 20:
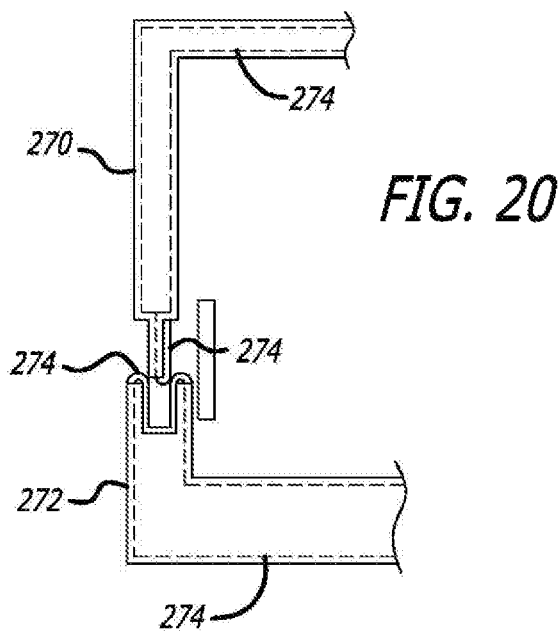
Figure 21:
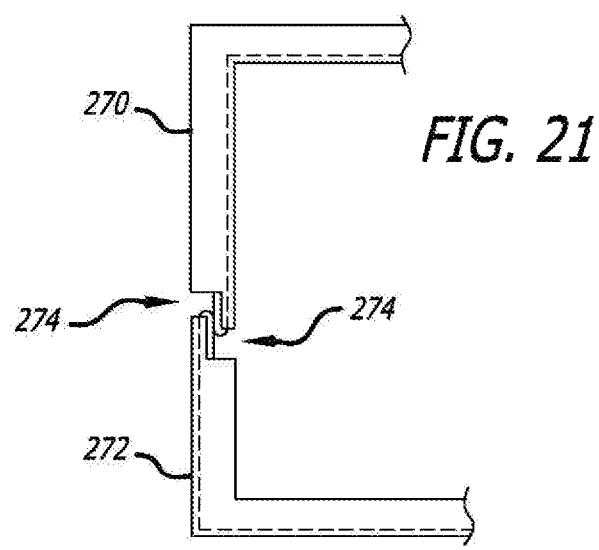
Figure 22:
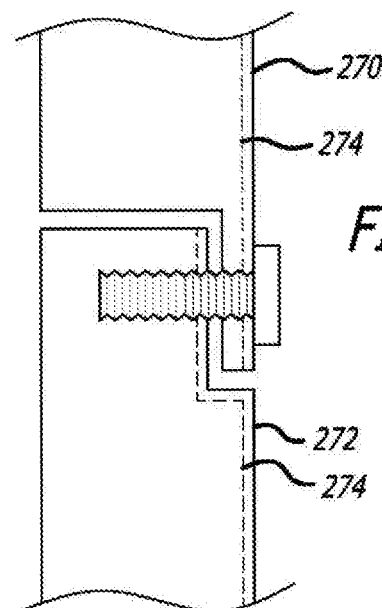
Figure 23:
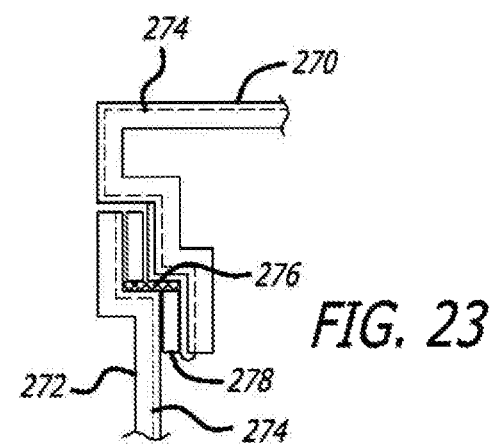

Referring to FIGS. 16-19, a layer of metal mesh is a surface of a wall that contacts the metal mesh of the wall with which it joins to form a tortuous path seal. In FIGS. 20-21, the metal mesh was fully embedded in the plastic but portions of mesh extending beyond the plastic edge have been bent around into the joint with the other piece and other piece's mesh to make electrical contact between the two. FIG. 22 shows a tortuous path seal where the electrical contact between the embedded metal meshes of the two parts are joined by a screw that comes in contact with both meshes and provides an electric contact between them. FIG. 23 has internally embedded metal mesh in the two parts that is bent around their contact point so that the mesh of each piece is in contact. The figure also shows the use of electrically conductive epoxy adhesive 276 and electrically conductive foam 278 to contribute to the RF shielding.

Figure 24:
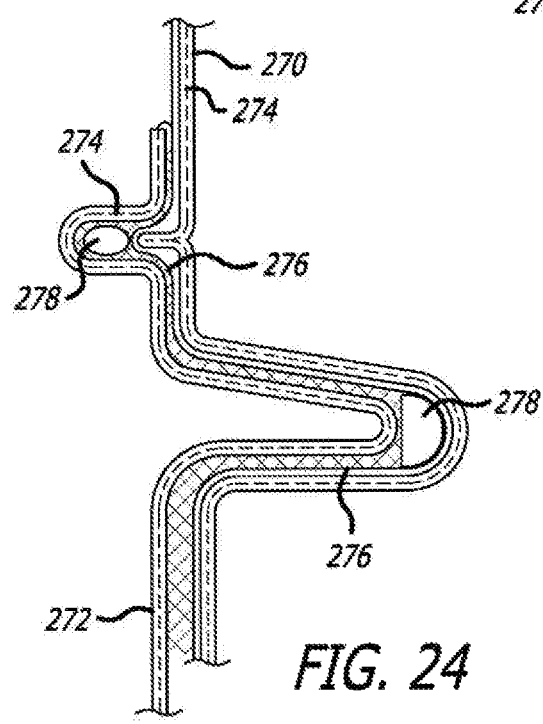
Figure 25:
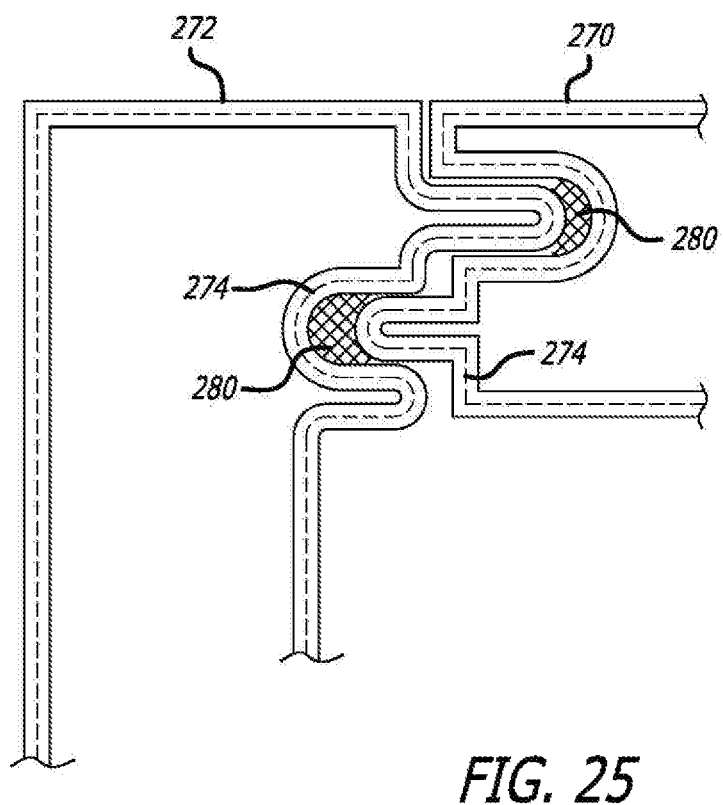

In FIG. 24, the metal mesh of the piece at the left extends beyond the edge of the plastic substrate 272 and that mesh has been bent around the areas where the two pieces join. Also, the metal mesh of the piece at the right is an external layer on the plastic that makes electrical contact with mesh of the piece on the left. Electrically conductive epoxy and foam are used in this embodiment also. In FIG. 25, electrically conductive metal mesh 274 is shown in dashed lines for the purpose of clarity in the drawing. In actuality, it is a layer on the plastic substrates of both pieces and is on the side that faces the other piece so that electric contact is made for the purpose of forming a Faraday cage as discussed above. FIG. 25 also shows the use of metal wool 280 positioned between the pieces to provide increased RF shielding.

Figure 26:
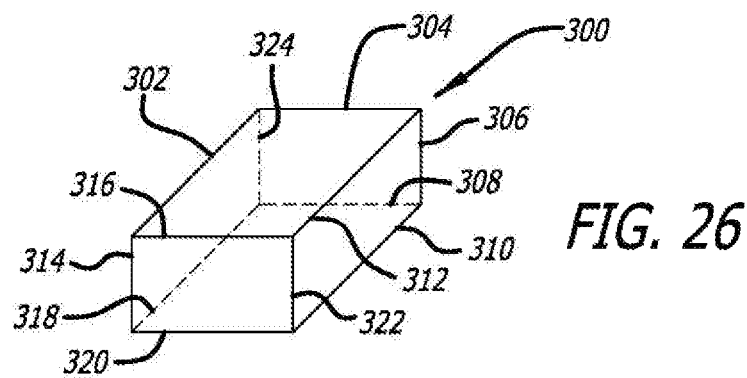
FIG. 26 presents a schematic diagram of an enclosure having six rectangular sides and showing the existence of twelve joint seams.

Turning now to FIG. 26, an enclosure 300 having a generally rectangular shape is shown. It can be seen that the enclosure 300 has six sides which are a front, a back, a top, a bottom, and two sides. Each of these sides is connected to four other sides. At each of these connection is a joint seam. There are therefore twelve joint seams. These are numerals 302, 304, 306, 308, 310, 312, 314, 316, 318, 320, 322, and 324. At each of these joint seams, the leakage of RF energy into and out of the space within the enclosure can occur.

Figure 27:
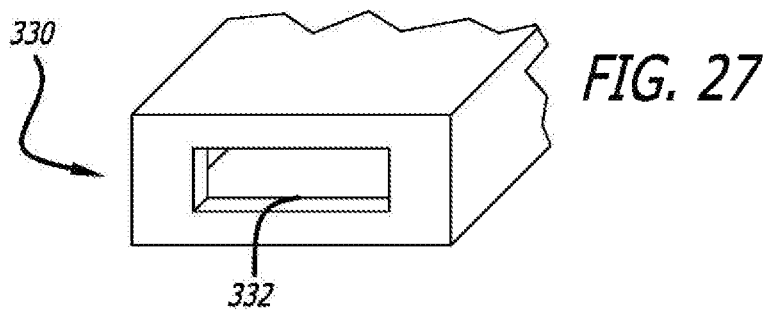
FIG. 27 shows in perspective view the front of an enclosure such as that shown in FIG. 26 with an opening formed in its front wall.

Referring briefly to FIG. 27, an abbreviated front perspective view of an enclosure 330 having an opening 332 in the front is shown. The enclosure is formed of six plastic walls, each of which comprises an electrically conductive component that is extensive with the wall. All the electrically conductive components are electrically connected with each other through one or more joining techniques described above and thus a Faraday cage has been formed. However this Faraday cage has the opening 332 through which RF leakage could occur.

Figure 28:
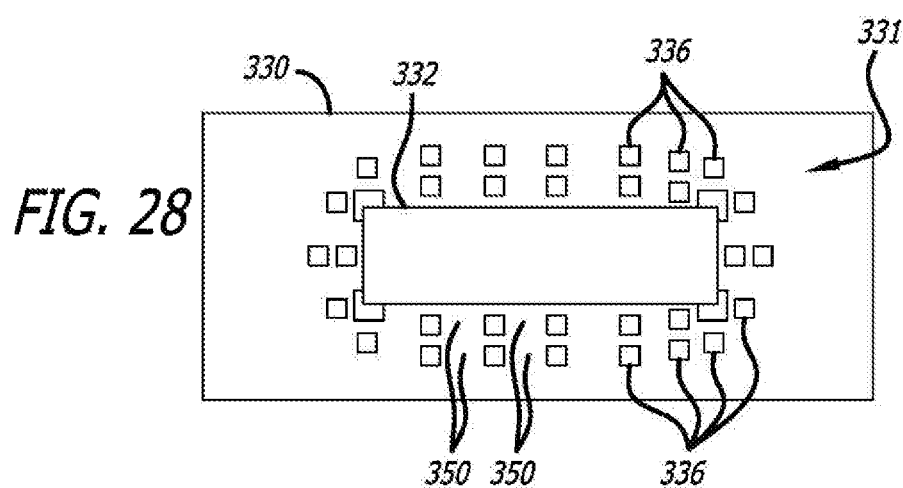
FIG. 28 presents a front view of the enclosure of FIG. 27 with a portion of a tortuous path formed about the opening.

This opening 332 may be used for a sliding drawer or for other purposes. The opening is meant to be covered and at the area of coverage, RF leakage can occur. FIG. 12 presents a means of establishing a tortuous path seal around the opening. In FIG. 28, a front perspective view of a portion of a tortuous path 331 is shown. There are dual rows of interspaced ridges 336 and channels 350. In order to preserve the clarity of the illustration, neither every ridge nor every channel has been indicated with a drawing numeral. When this portion of a tortuous path is combined with the portion of a tortuous path contained on the inside surface of the drawer wall 220 shown in FIG. 12, a tortuous path seal will be formed around the opening. Because all of the components shown in FIG. 12, including the ridges 336, channels 350, and foam are electrically conductive, a full Faraday cage will be formed when drawer wall 220 is pushed against the opening 332. The entire enclosure will be in electrical contact. Also, a tortuous path seal will also be formed around the opening 332 by means of moving the drawer wall portion of a tortuous path into contact with the complementary tortuous path portion of the opening 332.

Figure 29:
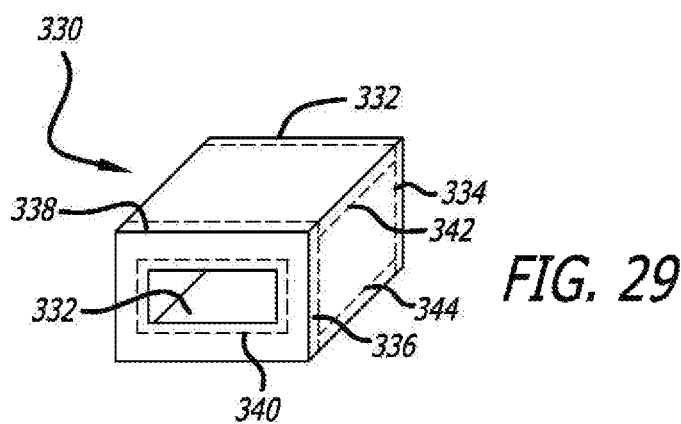
FIG. 29 is a schematic diagram of an enclosure similar to that of FIG. 26 showing the locations of tortuous path seals in dashed line at joint seams for shielding the seam from leakage of RF energy.

FIG. 29 schematically shows the locations of tortuous path seals 332, 334, 336, 338, 340, 342, and 344 of an enclosure at the seams where walls are joined together. Additionally, a portion of a tortuous path seal 340 is shown around the opening 332 on the front wall. When combined with a door or drawer wall having a complementary tortuous path, a tortuous path seal will then be formed as exist at other joint seams in the figure (332, 334, 336, 338, 340, 342).

The RF shielding includes thermoformed, pressure formed, etc. plastic components that include features providing a torturous path design necessary to ensure RF isolation. Torturous path features are incorporated into the plastic structures where the components are paired to create an RF-shielded enclosure with the RF isolation required to ensure that each enclosure provides not only a "Faraday cage" but also a tortuous path seal to result in the necessary isolation required to ensure that RFID tags in one enclosure are not read by the reader in an adjacent enclosure. Furthermore, one implementation of the RF-shielded plastic enclosure is composed of a small enclosure within a larger enclosure, where the small enclosure is RF-shielded by RF-shielding material positioned between the two enclosures. This implementation of the invention provides a means of easily insulating the smaller enclosure for those applications that require a cold storage area.

By incorporating the RF-shielding material into the plastic during the forming process and by designing the torturous path features into the plastic component shape, the invention provides a low cost, light weight alternative to metal enclosures. By providing a modular system whereby components can be paired to create drawers and enclosures of differing sizes, the invention eliminates the requirement for custom metal drawers and enclosures to meet the specific requirements of each tracking application.

Excluding upright refrigerated enclosures with side swinging doors, the two basic forms of small enclosures used to track medication using RFID technology are drawers and enclosures. In one aspect, RF-enabled drawers are used that are similar to a standard mechanical drawer in that a handle or knob is used to open the drawer thereby revealing a storage area. The drawer bottom, left side, right side, and back side are fabricated from a non-metallic material that is transparent to RF energy. The front of the drawer is made of a metallic or RF-shielding material as it forms the shielded front cover of the drawer enclosure. The drawer enclosure includes a false bottom in which the RFID reader and antennas are mounted, and above which the storage area of the drawer slides. The RFID tags attached to the items stored in the drawer are identified by the modulated RF energy transmitted by antennas mounted in the false bottom. The area under the false bottom, which exists to protect the reader and antennas, and the area surrounding the drawer storage area together make up the RF-enabled enclosure.

In one aspect, RF-shielded plastic components or shells form an enclosure when paired together. For example, in the case of the RF-enabled drawer of a fixed width and depth, one RF-shielded plastic bottom half is formed having an inner shell and an outer shell. The outer shell is RF-shielded by incorporating a metal screen or metal mesh onto or into the plastic during the forming process. The inner shell is not shielded, and is composed of an RF transparent material such as plastic, and serves as the false bottom of the RF-enabled drawer. The plastic bottom half also includes shielded torturous path features, around the top perimeter for attachment to the top half of the RF enclosure. The bottom half of the drawer enclosure may also include an opening or cut out in the front of the component to provide drawer access. The top half of the RF-shielded plastic drawer enclosure can be a single or double shell plastic component and includes at least one shell that is RF-shielded during the forming process. The plastic top half also includes shielded torturous path features, around the top perimeter for attachment to the bottom half of the RF enclosure. The top half of the drawer enclosure includes an opening or cut out in the front of the component to provide drawer access. Both top and bottom RF-shielded plastic halves or components include features around the perimeter of the drawer opening that facilitate the RF sealing of the drawer face plate to the drawer enclosure. One bottom RF-shielded plastic component can be fabricated to mate with several top RF-shielded plastic components to form RF drawer enclosures of differing heights. For example, an RF-enabled automated dispensing cabinet might require three different drawer heights for storing RF tagged items. The same bottom RF-shielded plastic component can be used for all three "different heights" drawer enclosures. The top RF-shielded plastic component defines the height of the drawer.

The invention provides a system of modular RF-shielded plastic components. The components are paired in various combinations to produce the enclosures necessary to track RFID tagged items in drawers and enclosures. The plastic components are shielded with a metal mesh that has been incorporated into the plastic structure during the forming process. The plastic components include features around the perimeter that facilitate the mechanical attachment of the two enclosure halves (i.e., top and bottom). The mechanical features also include the torturous path design required to isolate the enclosure for the purpose of containing the RF energy in the enclosure.

Another aspect includes the modular design of the shielded plastic components. The shielded plastic components are designed to mate in pairs to create enclosures or drawers of varying sizes. Since the RFID reader and read antennas are positioned under a false bottom in the base of both enclosures and drawers, one shielded plastic half or base can be designed for use in both drawers and enclosures of a specific width.

As used herein for convenience, the well-known Faraday cage or Faraday shield or Faraday cavity is an enclosure formed by electrically conductive material. A metal mesh of such material is one embodiment. Such an enclosure prevents RF energy generated inside the Faraday cage from leaking out and blocks out external static electric fields. A Faraday cage is not limited to square or rectangular sides and may take other forms.

As used herein, "embedded" means fixing an object firmly in a mass. In accordance with the usage herein, an object that is fully surrounded by the mass is embedded and an object that is only partially surrounded by the mass is embedded.

As used herein, "substrate" is used in a broad sense. Not only can the substrate have another component mounted to its exterior surface, it is also meant to include embedding another component fully within its interior, as well as embedding a portion of a component in its interior and mounting another portion of that same component to the substrate's exterior.

As used herein, "wool," "metal wool," "wire wool," "electrically-conductive wool," and "steel wool" refer to a bundle of electrically-conductive strands, and may be used interchangeably. The strands, which may also be described as filaments or fibers, may comprise fine carbon steel strands, low-grade carbon steel wire, stainless steel strands, aluminum strands, or other electrically-conductive material that are bunched into a fuzzy mass that resembles wool. The strands may vary in softness depending on their size and the application. The strands are configured to conduct electricity throughout the bundle, including transversely and longitudinally. There may or may not be backing material on either side or on one side of the bundle of electrically-conductive wool depending on the application.

A tortuous path seal described herein is also referred to as a tortuous seal and sometimes as a labyrinth seal.

Unless the context requires otherwise, throughout the specification and claims that follow, the word "comprise" and variations thereof, such as, "comprises" and "comprising," are to be construed in an open, inclusive sense, which is as "including, but not limited to."

While exemplary embodiments are described above, it is not intended that these embodiments describe all possible forms of the invention. Rather, the words used in the specification are words of description rather than limitation, and it is understood that various changes may be made without departing from the spirit and scope of the invention.

Additionally, the features of various implementing embodiments may be combined to form further embodiments of the invention.

What is claimed is:

1. A medical article storage container having an internal storage space, the storage container having radio-frequency (RF) shielding material arranged to attenuate the passage of RF energy out of and into the storage space, the container formed with a plurality of interconnected walls, the container comprising:
   a first wall of the plurality of interconnected walls comprising a substrate formed of an electrically non-conductive material, the first wall also comprising a joining edge configured to physically mate with another wall to form a joint seam between the two walls, the first wall also comprising an electrically conductive component that is coextensive with the first wall substrate and extends to the joining edge of the first wall at which location the electrically conductive component is exposed to electrically connect with an electrically conductive component of another wall at the joint seam, the first wall also comprising a first mating component of a tortuous path at the joining edge; and
   a second wall of the plurality of interconnected walls comprising a substrate that is formed of an electrically non-conductive material, the second wall also comprising a joining edge that is physically mated with the joining edge of the first wall to form a joint seam between the two walls, the second wall also comprising an electrically conductive component that is coextensive with the second wall substrate and extends to the joining edge of the second wall substrate at which location the electrically conductive component of the second wall is exposed, the electrically conductive component of the second wall being electrically connected to the electrically conductive component of the first wall at the joint seam, the second wall also comprising a second mating component of a tortuous path at the joining edge of the second wall, the second mating component mating with the first mating component of the first wall to thereby form a tortuous path seal at the joint seam to attenuate RF energy leaking out of and into the storage space;
   whereby the electrical connections of the first and second walls and the tortuous path seal provide further shielding from RF leakage.

2. The medical article storage container of claim 1 wherein the electrically conductive components of both the first and second walls are embedded into the substrate of their respective walls and are configured to extend beyond the joining edge of their respective walls and be exposed to electrically mate with an electrically conductive component of another wall at the joint seam thereby shielding the storage space from leaking RF energy.

3. The medical article storage container of claim 1 wherein the electrically conductive components of both the first and second walls are embedded into the substrate of their respective walls so that they form an outer surface of the wall which is configured to contact an electrically conductive component of another wall at the joint seam thereby shielding the storage space from leaking RF energy.

4. The medical article storage container of claim 1 wherein the electrically conductive components of both the first and second walls are disposed over an outer surface of the substrate of their respective walls and are configured to contact an electrically conductive component of another wall at the joint seam thereby shielding the storage space from leaking RF energy.

5. The medical article storage container of claim 1 wherein the tortuous path seal formed by the first and second walls comprises a tortuous path having two bends thereby increasing attenuation of leaking RF energy.

6. The medical article storage container of claim 1 wherein the tortuous path seal comprises a bend which is at an angle of ninety degrees.

7. The medical article storage container of claim 1 wherein the electrically-conductive component of the first wall comprises an electrically conductive metallic mesh embedded in the first wall substrate, the mesh having openings of a size selected in accordance with the frequency of the RF energy operating in the storage space to provide a predetermined amount of attenuation of the RF energy at the operating frequency.

8. The medical article storage container of claim 1 wherein the first and second walls have selectable sizes relative to each other wherein the first wall is used in a first storage container of a first size and the second wall is used in a second storage container of a second size that is different from the first storage container, wherein the first and second storage containers are modular containers that are connected together at joint seams of the first walls of the first storage container being connected to the second walls of the second storage container.

9. The medical article storage container of claim 8 wherein a joint seam at which two modular containers are connected together comprises a rib disposed over the joint seam, the rib comprising an RF energy channel having a bend thereby providing a tortuous path seal that attenuates RF energy leaking out of and into the storage space.

10. The medical article storage container of claim 1 wherein the tortuous path seal has a size selected to attenuate RF energy used for operation in the storage space.

11. The medical article storage container of claim 10 wherein the tortuous path seal comprises electrically conductive shielding foam which attenuates RF energy in the tortuous path seal thereby providing an electrical shield for the storage space.

12. The medical article storage container of claim 11 further comprising an electrically conductive adhesive applied to the electrically conductive shielding foam to secure it in place in the tortuous path seal.

13. The medical article storage container of claim 1 wherein the tortuous path seal has a size selected to attenuate RF energy used for operation in the storage space, the tortuous path seal further comprising metal wool shielding located within the tortuous path seal which attenuates RF energy in the tortuous path seal thereby providing an electrical shield for the storage space.

14. The medical article storage container of claim 1 wherein the substrates of the first and second walls are formed of a plastic having a selected coefficient of electrical conductivity whereby a lighter wall is provided.

15. The medical article storage container of claim 1 wherein the first wall comprises an opening providing access to the internal storage space, the medical article storage container also comprising a door located at an outer surface of the first wall and covering the opening at one position and uncovering the opening in a second position, the door comprising electrically conductive material on an inner surface coextensive with the size of the door to electrically mate with the electrically conductive component of the first wall to provide an RF shield across the opening of the first wall, the first wall further comprising a first component of a tortuous path located about the opening of the first wall, and the door comprising a second component of a tortuous path configured to mate with the first component of the tortuous path of the first wall to create a tortuous path seal when the door is in the closed position such that the tortuous path seal is completed and the tortuous path seal is formed when the door is in the closed position.

16. The medical article storage container of claim 15 wherein the tortuous path seal has a size selected to attenuate energy at an operating frequency in the storage space.

17. The medical article storage container of claim 15 further comprising a drawer slidably located in the opening of the first wall and movable into and out of the storage space, the drawer having a front wall that is larger than the opening in the first wall of the container which comprises the door, the front wall of the drawer being movable to a closed position in relation to the medical article storage container at which the front wall of the drawer moves into contact with the first wall and covers the opening;
    wherein the drawer is formed of an electrically nonconductive material;
    wherein the drawer front wall includes an electrically conductive component coexistent with the front wall and configured so that when the drawer is in the closed position, the electrically conductive component of the front wall of the drawer is placed into physical and electrical contact with the electrically conductive component of the first wall in which the opening is formed;
    wherein the front wall of the drawer further includes a first component of a tortuous path located about edges of the front wall of the drawer;
    wherein the first wall of the medical article storage container includes a second component of a tortuous path located about the opening in the first wall such that when the drawer is closed, the two components of the tortuous path mate and form a tortuous path seal thereby shielding the storage space from leakage of RF energy out of and into the storage space.

18. The medical article storage container of claim 15 wherein the tortuous path seal located about the front wall of the drawer has a bend of ninety degrees to attenuate electrical energy.

19. The medical article storage container of claim 1 further comprising a first container module having a false bottom under which are located an RFID reader and an RFID probe and antenna, and comprising a second module containing the internal storage space coupled to the first module, the RFID reader and RFID probe and antenna configured to be usable with different sizes of second module attached to the first module of the container.

20. The medical article storage container of claim 19 wherein the second module is attached to the first module at a joint seam, the container further comprising an RFID shielding rib located over the joint seam and providing a tortuous path seal at the joint seam.

21. A method of shielding an internal storage space of a medical article storage container from RF energy leakage out of and into the internal storage space, the storage container having radio-frequency (RF) shielding material arranged to attenuate the passage of RF energy out of and into the internal storage space, the method comprising:
    surrounding the internal storage space with a plurality of interconnected walls, each of the walls having a plastic substrate with an embedded electrically conductive component that is coextensive with the substrate;
    connecting together the coextensive electrically conductive components of adjacent walls at joint seams, wherein each wall has a joining edge configured to mate physically and electrically with a joining edge of another wall to form a joint seam, thereby providing electrically conducting walls located completely around the internal storage space to attenuate RF energy and shield the internal storage space from leakage of RF energy; and
    forming an RF tortuous path seal at each joint seam through connecting together a first component of an RF tortuous path located at a first wall at the joint seam with a second component of an RF tortuous path located at a second wall at the same joint seam as the first wall, wherein connecting together the first and second components of the RF tortuous path provides an RF tortuous path seal that attenuates RF energy;
    whereby the internal storage space storage area is shielded against the leakage of RF energy out.

22. The method of shielding an internal storage space of a medical article storage container from RF energy leakage of claim 21 wherein the step of forming an RF tortuous path seal comprises forming a bend of ninety degrees in the tortuous path seal.

23. The method of shielding an internal storage space of a medical article storage container from RF energy leakage of claim 21 wherein the walls comprise electrically conductive mesh embedded in the substrate of the walls, comprising the step of selecting the mesh to have openings of a size selected in accordance with the frequency of the RF energy operating in the storage space to provide a predetermined amount of attenuation of RF energy at the operating frequency of the storage space.

24. The method of shielding an internal storage space of a medical article storage container from RF energy leakage of claim 21 further comprising the step of selecting the sizes of the walls relative to each other wherein a first wall is used in a first storage container of a first size and a second wall is used in a second storage container of a second size that is different from the first storage container, and connecting together the first and second storage containers, which are modular containers, at joint seams of the walls of the first storage container being connected to the second walls of the second storage container.

25. The method of shielding an internal storage space of a medical article storage container from RF energy leakage of claim 21 further comprising selecting the size of the tortuous path seal to attenuate energy at an operating frequency in the storage space.

26. A medical article storage container having an internal storage space for use with radio-frequency (RF) energy at an operating frequency, the storage container having RF shielding material arranged to attenuate the passage of RF energy at the operating frequency out of and into the storage space, the container formed with a plurality of interconnected walls, the container comprising:
    a first wall of the plurality of interconnected walls comprising a substrate formed of an electrically non-conductive material, the first wall also comprising a joining edge configured to physically mate with another wall to form a joint seam between the two walls, the first wall also comprising an electrically conductive component that is coextensive with the first wall substrate and extends to the joining edge of the first wall at which location the electrically conductive component is exposed to electrically connect with an electrically conductive component of another wall at the joint seam, the first wall also comprising a first mating component of a tortuous path at the joining edge; and a second wall of the plurality of interconnected walls comprising a substrate that is formed of an electrically non-conductive material, the second wall also comprising a joining edge that is physically mated with the joining edge of the first wall to form a joint seam between the two walls, the second wall also comprising an electrically conductive component that is coextensive with the second wall substrate and extends to the joining edge of the second wall substrate at which location the electrically conductive component of the second wall is exposed, the electrically conductive component of the second wall being electrically connected to the electrically conductive component of the first wall at the joint seam, the second wall also comprising a second mating component of a tortuous path at the joining edge of the second wall, the second mating component mating with the first mating component of the first wall to thereby form a tortuous path seal at the joint seam to attenuate RF energy leaking out of and into the storage space;

wherein the tortuous path seal has a size selected to attenuate RF energy used for operation in the storage space;

wherein the first and second walls have selectable sizes relative to each other; the first wall is used in a first storage container of a first size and the second wall is used in a second storage container of a second size that is different from the first storage container, wherein the first and second storage containers are modular containers that are connected together at joint seams of the first walls of the first storage container being connected to the second walls of the second storage container;

whereby the electrical connections of the first and second walls and the tortuous path seal provide further shielding from RF leakage.

27. The medical article storage container of claim 26 wherein the electrically conductive components of both the first and second walls are embedded into the substrate of their respective walls and are configured to extend beyond the joining edge of their respective walls and be exposed to electrically mate with an electrically conductive component of another wall at the joint seam thereby shielding the storage space from leaking RF energy.

28. The medical article storage container of claim 26 wherein the electrically conductive components of both the first and second walls are embedded into the substrate of their respective walls so that they form an outer surface of the wall which is configured to contact an electrically conductive component of another wall at the joint seam thereby shielding the storage space from leaking RF energy.

29. The medical article storage container of claim 28 wherein the tortuous path seal further comprises electrically conductive adhesive applied to the foam at a selected position in the tortuous path seal, the electrically conductive adhesive holding the foam permanently in the selected position and contributing to the electrical shield of the storage space.

30. The medical article storage container of claim 26 wherein the electrically conductive components of both the first and second walls are disposed over an outer surface of the substrate of their respective walls and are configured to contact an electrically conductive component of another wall at the joint seam thereby shielding the storage space from leaking RF energy.

31. The medical article storage container of claim 26 wherein the tortuous path seal formed by the first and second walls comprises a tortuous path having two bends thereby increasing attenuation of leaking RF energy.

32. The medical article storage container of claim 26 wherein the tortuous path seal comprises a bend which is at an angle of ninety degrees.

* * * * *